(12) United States Patent
Tabb et al.

(10) Patent No.: US 11,300,519 B2
(45) Date of Patent: Apr. 12, 2022

(54) REAGENTS AND METHODS FOR DETECTING INFECTIOUS DISEASES

(71) Applicant: Ionica Sciences, Ithaca, NY (US)

(72) Inventors: Joel S. Tabb, Slaterville Springs, NY (US); Omar Green, New York, NY (US)

(73) Assignee: Ionica Sciences, Ithaca, NY (US)

( * ) Notice: Subject to any disclaimer, the term of this patent is extended or adjusted under 35 U.S.C. 154(b) by 0 days.

(21) Appl. No.: 15/552,196

(22) PCT Filed: Feb. 19, 2016

(86) PCT No.: PCT/US2016/018600
§ 371 (c)(1),
(2) Date: Aug. 18, 2017

(87) PCT Pub. No.: WO2016/134214
PCT Pub. Date: Aug. 25, 2016

(65) Prior Publication Data
US 2018/0217068 A1    Aug. 2, 2018

Related U.S. Application Data

(60) Provisional application No. 62/263,995, filed on Dec. 7, 2015, provisional application No. 62/264,088, filed on Dec. 7, 2015, provisional application No. 62/118,453, filed on Feb. 19, 2015.

(51) Int. Cl.
| | | |
|---|---|---|
| G01N 21/65 | (2006.01) | |
| G01N 33/58 | (2006.01) | |
| C12N 15/115 | (2010.01) | |

(52) U.S. Cl.
CPC ......... *G01N 21/658* (2013.01); *C12N 15/115* (2013.01); *G01N 33/58* (2013.01); *C12N 2310/16* (2013.01)

(58) Field of Classification Search
CPC ..... G01N 15/658; G01N 33/58; C12N 15/115
See application file for complete search history.

(56) References Cited

U.S. PATENT DOCUMENTS

| | | |
|---|---|---|
| 2005/0227252 A1 | 10/2005 | Moon et al. |
| 2009/0298197 A1* | 12/2009 | Natan ............... C12Q 1/6818 436/501 |
| 2010/0105053 A1 | 4/2010 | Cho et al. |
| 2011/0275061 A1 | 11/2011 | Weidemaier et al. |
| 2012/0302940 A1* | 11/2012 | Ray ................. A61K 49/0065 604/20 |
| 2013/0023435 A1 | 1/2013 | Kho et al. |
| 2014/0302492 A1 | 10/2014 | Blackburn et al. |
| 2016/0166186 A1* | 6/2016 | Ferguson ............ A61B 5/14546 600/352 |

FOREIGN PATENT DOCUMENTS

| | | |
|---|---|---|
| WO | WO-2007/059514 A2 | 5/2007 |
| WO | WO-2008/116093 A2 | 9/2008 |

OTHER PUBLICATIONS

Baker et al (J. Am. Chem. Soc 128:3138-3139, 2006) (Year: 2006).*
Kim et al. (Adv. Mater. 2011, 23, 4152-4156) (Year: 2011).*
Xiao et al (Angew. Chem. Int. Ed. 2005, 44, 5456-5459) (Year: 2005).*
Extended European Search Report for ER Application No. 16753111.0 dated Jun. 13, 2018.
Huh et al., "Aptamer Based Surface Enhanced Raman Scattering Detection of Vasopressin Using Multilayer Nanotube Arrays," Biosensors and Bioelectronics, 25(5): 1240-1243 (2010).
Kim et al., "Aptamer-Mediated Surface-Enhanced Raman Spectroscopy Intensity Amplification," Nano Letters, 10(10): 4181-4185 (2010).
Yang et al., "Surface-Enhanced Raman Spectroscopy Based Quantitative Bioassay on Aptamer-Functionalized Nanopillars Using Large-Area Raman Mapping," ACS Nano, 7(6):5350-5359 (2013).
Fabris et al., "Aptatag-based multiplexed assay for protein detection by surface-enhanced Raman spectroscopy," Small, 6(14): 1550-1557 (2010).
International Search Report and Written Opinion for International Application No. PCT/US2016/018600, dated Jun. 24, 2016.
Chen et al., "A new aptameric biosensor for cocaine based on surface-enhanced raman scattering spectroscopy," Chemistry—A European Journal, 14(27):8374-8382 (2008).

* cited by examiner

*Primary Examiner* — Richard A Schnizer
(74) *Attorney, Agent, or Firm* — Foley Hoag LLP

(57) ABSTRACT

Provided herein are surface enhanced Raman scattering (SERS)-active reagents and methods for detecting one or more analyte in a sample. Said SERS-active reagents are adaptable, sensitive, and easy-to-use in the diagnosis of infectious diseases in a patient, or the detection of toxins, bacteria, viruses, pathogens, hormones, cytokines, antigens, antibodies or illicit drugs in a biological sample. Such methods may be handled by police, soldiers, or health care workers in the field, and do not require specialized training.

11 Claims, 14 Drawing Sheets

Specification includes a Sequence Listing.

NaCl concentration (mM)

Wavenumber (cm⁻¹)

Wavenumber (cm⁻¹)

Wavenumber (cm⁻¹)

SEQUENCE LISTING

<160> NUMBER OF SEQ ID NOS: 84

<210> SEQ ID NO 1

-continued

```
<211> LENGTH: 107
<212> TYPE: DNA
<213> ORGANISM: Artificial Sequence
<220> FEATURE:
<223> OTHER INFORMATION: synthetic aptamer
<220> FEATURE:
<221> NAME/KEY: misc_feature
<222> LOCATION: (34)..(73)
<223> OTHER INFORMATION: n is a, c, g, or t

<400> SEQUENCE: 1
acactctttc cctacacgac gctcttccga tctnnnnnnn nnnnnnnnnn nnnnnnnnnn      60
nnnnnnnnnn nnnagatcgg aagagcacac gtctgaactc cagtcac                  107

<210> SEQ ID NO 2
<211> LENGTH: 64
<212> TYPE: DNA
<213> ORGANISM: Artificial Sequence
<220> FEATURE:
<223> OTHER INFORMATION: synthetic primer

<400> SEQUENCE: 2
caagcagaag acggcatacg agatattggc gtgactggag ttcagacgtg tgctcttccg      60
atct                                                                  64

<210> SEQ ID NO 3
<211> LENGTH: 64
<212> TYPE: DNA
<213> ORGANISM: Artificial Sequence
<220> FEATURE:
<223> OTHER INFORMATION: synthetic primer

<400> SEQUENCE: 3
caagcagaag acggcatacg agatgatctg gtgactggag ttcagacgtg tgctcttccg      60
atct                                                                  64

<210> SEQ ID NO 4
<211> LENGTH: 64
<212> TYPE: DNA
<213> ORGANISM: Artificial Sequence
<220> FEATURE:
<223> OTHER INFORMATION: synthetic primer

<400> SEQUENCE: 4
caagcagaag acggcatacg agattacaag gtgactggag ttcagacgtg tgctcttccg      60
atct                                                                  64

<210> SEQ ID NO 5
<211> LENGTH: 64
<212> TYPE: DNA
<213> ORGANISM: Artificial Sequence
<220> FEATURE:
<223> OTHER INFORMATION: synthetic primer

<400> SEQUENCE: 5
caagcagaag acggcatacg agatctctac gtgactggag ttcagacgtg tgctcttccg      60
atct                                                                  64

<210> SEQ ID NO 6
<211> LENGTH: 39
<212> TYPE: DNA
<213> ORGANISM: Artificial Sequence
<220> FEATURE:
<223> OTHER INFORMATION: synthetic oligonucleotide
```

-continued

<400> SEQUENCE: 6
atgcaaatta gcataagcag cttgcagacc cataatgtc                                    39

<210> SEQ ID NO 7
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 7
atagtgttat taatatcaag ttgggggagc acattgtag                                    39

<210> SEQ ID NO 8
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 8
cttgtttacg aattaaatcg aagtggactg ctggcggaa                                    39

<210> SEQ ID NO 9
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 9
taaacgtgac gatgagggac ataaaaagta aaaatgtct                                    39

<210> SEQ ID NO 10
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 10 tttaaagcg ccgtggatgc ctgaccgtac cgaggctaa                                     39

<210> SEQ ID NO 11
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 11
agttgccata caaaacaggg tcgccagcaa tatcggtat                                    39

<210> SEQ ID NO 12
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 12
tagccacata gaaaccaaca gccatataac tggtagctt                                    39

<210> SEQ ID NO 13

```
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 13
cataatgtca atagatgtgg tagaagtcgt catttggcg                              39

<210> SEQ ID NO 14
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 14
taataacctg attcagcgaa accaatccgc ggcatttag                              39

<210> SEQ ID NO 15
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 15
cacagtcctt gacggtataa taaccaccat catggcgac                              39

<210> SEQ ID NO 16
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 16
gcggcggcaa gttgccatac aaaacagggt cgccagcaa                              39

<210> SEQ ID NO 17
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 17
tatttaactg gcggcgattg cgtacccgac gaccaaaat                              39

<210> SEQ ID NO 18
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 18
aagagcagaa gcaataccgc cagcaatagc accaaacat                              39

<210> SEQ ID NO 19
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 19
```

```
cagcgaaacc aatccgcggc atttagtagc ggtaaagtt                                  39
```

<210> SEQ ID NO 20
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 20

```
tatggctaaa gctggtaaag gacttcttga aggtacgtt                                  39
```

<210> SEQ ID NO 21
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 21

```
atggaaatga agacggccat tagctgtacc atactcagg                                  39
```

<210> SEQ ID NO 22
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 22

```
ctctttagtc gcagtaggcg gaaaacgaac aagcgcaag                                  39
```

<210> SEQ ID NO 23
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 23

```
acgaaagacc aggtatatgc acaaaatgag atgcttgct                                  39
```

<210> SEQ ID NO 24
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 24

```
catataactg gtagctttaa gcggctcacc tttagcatc                                  39
```

<210> SEQ ID NO 25
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 25

```
tgaaaccaac ataaacatta ttgcccggcg tacggggaa                                  39
```

<210> SEQ ID NO 26
<211> LENGTH: 39
<212> TYPE: DNA

<213> ORGANISM: Artificial Sequence
<220> FEATURE:
<223> OTHER INFORMATION: synthetic oligonucleotide

<400> SEQUENCE: 26
tttagccata gcaccagaaa caaaactagg gacggcctc                                  39

<210> SEQ ID NO 27
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 27
tttagtcgca gtaggcggaa acgaacaag cgcaagagt                                   39

<210> SEQ ID NO 28
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 28
aagcaccttt agcgttaagg tactgaatct ctttagtcg                                  39

<210> SEQ ID NO 29
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 29
attctttagc tcctagacct ttagcagcaa ggtccatat                                  39

<210> SEQ ID NO 30
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 30
attggtatca gggttaatcg tgccaagaaa agcggcatg                                  39

<210> SEQ ID NO 31
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 31
cagatattga agcagaacgc aaaaagagag atgagattg                                  39

<210> SEQ ID NO 32
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 32
aaaaacgata aaccaaccat cagcatgagc ctgtcgcat                                  39

<210> SEQ ID NO 33
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 33
cagtaggcgg aaaacgaaca agcgcaagag taaacatag                            39

<210> SEQ ID NO 34
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 34
cctcacttaa gtggctggag acaaataatc tctttaata                            39

<210> SEQ ID NO 35
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 35
gaagtgccag cctgcaacgt accttcaaga agtcccttta                           39

<210> SEQ ID NO 36
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 36
gcatcatctt gattaagctc attagggtta gcctcggta                            39

<210> SEQ ID NO 37
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 37
ggatttgaga atcaaaaaga gcttactaaa atgcaactg                            39

<210> SEQ ID NO 38
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 38
tgaccagcaa ggaagccaag atgggaaagg tcatgcggc                            39

<210> SEQ ID NO 39
<211> LENGTH: 39
<212> TYPE: DNA
<213> ORGANISM: Artificial Sequence
<220> FEATURE:

<223> OTHER INFORMATION: synthetic oligonucleotide

<400> SEQUENCE: 39
tttcctgctc ctgttgagtt tattgctgcc gtcattgct                            39

<210> SEQ ID NO 40
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 40
ggtcagtagc aatccaaact ttgttactcg tcagaaaat                            39

<210> SEQ ID NO 41
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 41
aaatagttgt tatagatatt caaataaccc tgaaacaaa                            39

<210> SEQ ID NO 42
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 42
gggagggtag tcggaaccga agaagactca aagcgaacc                            39

<210> SEQ ID NO 43
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 43
gtcatttggc gagaaagctc agtctcagga ggaagcgga                            39

<210> SEQ ID NO 44
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 44
cggcgtacgg ggaaggacgt caatagtcac acagtcctt                            39

<210> SEQ ID NO 45
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 45
ataatctctt taataacctg attcagcgaa accaatccg                            39

<210> SEQ ID NO 46
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 46
attagctgta ccatactcag gcacacaaaa atactgata                          39

<210> SEQ ID NO 47
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 47
ttgttataga tattcaaata accctgaaac aaatgctta                          39

<210> SEQ ID NO 48
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 48
tgtagcgaac tgcgatgggc atactgtaac cataaggcc                          39

<210> SEQ ID NO 49
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 49
agcttactaa aatgcaactg gacaatcaga aagagattg                          39

<210> SEQ ID NO 50
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 50
tcaatagcag gtttaagagc ctcgatacgc tcaaagtca                          39

<210> SEQ ID NO 51
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 51
ccgcttcggc gttataacct cacactcaat cttttatca                          39

<210> SEQ ID NO 52
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 52
tatcagggtt aatcgtgcca agaaaagcgg catggtcaa                       39

<210> SEQ ID NO 53
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 53
caccaaacat aaatcacctc acttaagtgg ctggagaca                       39

<210> SEQ ID NO 54
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 54
tccatatctg acttttttgtt aacgtattta gccacatag                      39

<210> SEQ ID NO 55
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 55
aataatgttt atgttggttt catggtttgg tctaactttt                      39

<210> SEQ ID NO 56
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 56
acgttaacaa aaagtcagat atggaccttg ctgctaaag                       39

<210> SEQ ID NO 57
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 57
acgttggctg acgaccgatt agaggcgttt tatgataat                       39

<210> SEQ ID NO 58
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 58
catggtggcg aataagtacg cgttcttgca aatcaccag                       39

<210> SEQ ID NO 59
<211> LENGTH: 39

<212> TYPE: DNA
<213> ORGANISM: Artificial Sequence
<220> FEATURE:
<223> OTHER INFORMATION: synthetic oligonucleotide

<400> SEQUENCE: 59
cgggcaataa tgtttatgtt ggtttcatgg tttggtcta                    39

<210> SEQ ID NO 60
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 60
gcgatgggca tactgtaacc ataaggccac gtattttgc                    39

<210> SEQ ID NO 61
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 61
aacaaaaagt cagatatgga ccttgctgct aaaggtcta                    39

<210> SEQ ID NO 62
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 62
acgcggcaca gaatgtttat aggtctgttg aacacgacc                    39

<210> SEQ ID NO 63
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 63
atggtggcga ataagtacgc gttcttgcaa atcaccaga                    39

<210> SEQ ID NO 64
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 64
ccgccagtta aatagcttgc aaaatacgtg gccttatgg                    39

<210> SEQ ID NO 65
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 65
ttttaaagcg ccgtggatgc ctgaccgtac cgaggctaa                                    39

<210> SEQ ID NO 66
<211> LENGTH: 78
<212> TYPE: DNA
<213> ORGANISM: Artificial Sequence
<220> FEATURE:
<223> OTHER INFORMATION: synthetic oligonucleotide

<400> SEQUENCE: 66
taacagatac aaactcatca cgaacgtcag aagcagcctt aacagataca aactcatcac           60
gaacgtcaga agcagcct                                                         78

<210> SEQ ID NO 67
<211> LENGTH: 90
<212> TYPE: DNA
<213> ORGANISM: Artificial Sequence
<220> FEATURE:
<223> OTHER INFORMATION: synthetic aptamer

<400> SEQUENCE: 67
catgacaccg tacctgctct aataagcacg ccagggacta ttagatcgga atagcacacg           60
tctgaactcc aagcacgcca gggactatta                                            90

<210> SEQ ID NO 68
<211> LENGTH: 90
<212> TYPE: DNA
<213> ORGANISM: Artificial Sequence
<220> FEATURE:
<223> OTHER INFORMATION: synthetic aptamer

<400> SEQUENCE: 68
catgacaccg tacctgctct aataagcacg ccagggacta ttagatcgga agagcacacg           60
tgtgaactcc aagcacgcca gggactatta                                            90

<210> SEQ ID NO 69
<211> LENGTH: 90
<212> TYPE: DNA
<213> ORGANISM: Artificial Sequence
<220> FEATURE:
<223> OTHER INFORMATION: synthetic aptamer

<400> SEQUENCE: 69
catgacaccg tacctgctct acgagattca agcactccag ggactattag atcggaagag           60
cacacgtctg aagcacgcca gggactatta                                            90

<210> SEQ ID NO 70
<211> LENGTH: 90
<212> TYPE: DNA
<213> ORGANISM: Artificial Sequence
<220> FEATURE:
<223> OTHER INFORMATION: synthetic aptamer

<400> SEQUENCE: 70
catgacaccg tacctgctct acgagattca agcacgccag ggattattag atcggaagag           60
cacacgtctg aagcacgcca gggactatta                                            90

<210> SEQ ID NO 71
<211> LENGTH: 90
<212> TYPE: DNA
<213> ORGANISM: Artificial Sequence
<220> FEATURE:
<223> OTHER INFORMATION: synthetic aptamer

<400> SEQUENCE: 71
catgacaccg tacctgctct tgcttttcgt gcgcgcataa aatactttga tactgtgccg      60
gatgaaagcg aagcacgcca gggactatta                                       90

<210> SEQ ID NO 72
<211> LENGTH: 90
<212> TYPE: DNA
<213> ORGANISM: Artificial Sequence
<220> FEATURE:
<223> OTHER INFORMATION: synthetic aptamer

<400> SEQUENCE: 72
catgacaccg tacctgctct tgcttttcgt gcgcgcataa ataccttga tactgtgccg       60 tatgaaagcg aagcacgcca gggactatta                                       90

<210> SEQ ID NO 73
<211> LENGTH: 90
<212> TYPE: DNA
<213> ORGANISM: Artificial Sequence
<220> FEATURE:
<223> OTHER INFORMATION: synthetic aptamer

<400> SEQUENCE: 73
catgacaccg tacctgctct gcggtgctgt atcgtcgttt aggctgttac cagggccacc      60
ggacagaggt aagcacgcca gggactatta                                       90

<210> SEQ ID NO 74
<211> LENGTH: 90
<212> TYPE: DNA
<213> ORGANISM: Artificial Sequence
<220> FEATURE:
<223> OTHER INFORMATION: synthetic aptamer

<400> SEQUENCE: 74
catgacaccg tacctgctct cgtatagatc ctctcgcgct tcggttttta gaagtattca      60
aggtatcatc aagcacgcca gggactatta                                       90

<210> SEQ ID NO 75
<211> LENGTH: 90
<212> TYPE: DNA
<213> ORGANISM: Artificial Sequence
<220> FEATURE:
<223> OTHER INFORMATION: synthetic aptamer

<400> SEQUENCE: 75
catgacaccg tacctgctct gatcagcctg gtcaacgggt ggtcctgtgc caagctcgaa      60
aattcgccga aagcacgcca gggactatta                                       90

<210> SEQ ID NO 76
<211> LENGTH: 90
<212> TYPE: DNA
<213> ORGANISM: Artificial Sequence
<220> FEATURE:
<223> OTHER INFORMATION: synthetic aptamer

<400> SEQUENCE: 76
catgacaccg tacctgctct tggagctaga gagccggtga tcgaaattct ggatgtttct      60
gacgtttgct aagcacgcca gggactatta                                       90

<210> SEQ ID NO 77

```
<211> LENGTH: 90
<212> TYPE: DNA
<213> ORGANISM: Artificial Sequence
<220> FEATURE:
<223> OTHER INFORMATION: synthetic aptamer

<400> SEQUENCE: 77
catgacaccg tacctgctct accccggaaa tgattagcca ttgtggtact catctgggca      60
gtcagcacat aagcacgcca gggactatta                                      90

<210> SEQ ID NO 78
<211> LENGTH: 90
<212> TYPE: DNA
<213> ORGANISM: Artificial Sequence
<220> FEATURE:
<223> OTHER INFORMATION: synthetic aptamer

<400> SEQUENCE: 78
catgacaccg tacctgctct ttaacccctc gcggaggtgt acacgggcct acataatcct      60
ccgaggttcc aagcacgcca gggactatta                                      90

<210> SEQ ID NO 79
<211> LENGTH: 90
<212> TYPE: DNA
<213> ORGANISM: Artificial Sequence
<220> FEATURE:
<223> OTHER INFORMATION: synthetic aptamer

<400> SEQUENCE: 79
catgacaccg tacctgctct ttacgtttgg gacgtctggc gaagccacca caagctagcc      60
ctccaattta aagcacgcca gggactatta                                      90

<210> SEQ ID NO 80
<211> LENGTH: 90
<212> TYPE: DNA
<213> ORGANISM: Artificial Sequence
<220> FEATURE:
<223> OTHER INFORMATION: synthetic aptamer

<400> SEQUENCE: 80
catgacaccg tacctgctct ttgatcatca cggcacactc attacggttg gatatactag      60
tccggttaga aagcacgcca gggactatta                                      90

<210> SEQ ID NO 81
<211> LENGTH: 90
<212> TYPE: DNA
<213> ORGANISM: Artificial Sequence
<220> FEATURE:
<223> OTHER INFORMATION: synthetic aptamer

<400> SEQUENCE: 81
catgacaccg tacctgctct cccttctgac tggatgccgg atctgggccg attttgttcg      60
cgccccgccc aagcacgcca gggactatta                                      90

<210> SEQ ID NO 82
<211> LENGTH: 90
<212> TYPE: DNA
<213> ORGANISM: Artificial Sequence
<220> FEATURE:
<223> OTHER INFORMATION: synthetic aptamer

<400> SEQUENCE: 82
catgacaccg tacctgctct ttccgctggt tccacgtggt cccgcgtagg ttcgtgtgcg      60
```

```
cgcaaaatcc aagcacgcca gggactatta                                          90

<210> SEQ ID NO 83
<211> LENGTH: 90
<212> TYPE: DNA
<213> ORGANISM: Artificial Sequence
<220> FEATURE:
<223> OTHER INFORMATION: synthetic aptamer

<400> SEQUENCE: 83
catgacaccg tacctgctct gcccctgcgt gccgcagtca atcaccatgt tgttattacg         60
gactacctgg aagcacgcca gggactatta                                          90

<210> SEQ ID NO 84
<211> LENGTH: 90
<212> TYPE: DNA
<213> ORGANISM: Artificial Sequence
<220> FEATURE:
<223> OTHER INFORMATION: synthetic aptamer

<400> SEQUENCE: 84
catgacaccg tacctgctct ccggtacgat aggggttgag ttggacacac tgcctggtta         60
aattgtgcag aagcacgcca gggactatta                                          90
```

REAGENTS AND METHODS FOR DETECTING INFECTIOUS DISEASES

CROSS REFERENCE TO RELATED APPLICATIONS

This application is a U.S. national stage of International Application PCT/US16/18600, filed Feb. 19, 2016, which claims priority to U.S. Provisional Application No. 62/118,453, filed Feb. 19, 2015, U.S. Provisional Application No. 62/263,995, filed Dec. 7, 2015, and U.S. Provisional Application No. 62/264,088, filed Dec. 7, 2015, the contents of each are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 31, 2016, is named ISS125_ST25.txt and is 19 KB in size.

BACKGROUND

The present invention is directed to products for and methods of detecting analytes bound by functionalized aptamers using surface-enhanced Raman scattering (SERS). The system is composed of three basic parts: a SERS-active surface, an aptamer, and a Raman-active marker attached to the aptamer. The functionalized aptamer is covalently or non-covalently attached to the SERS-active surface. When this complex is contacted with a sample containing the aptamer binding target (i.e., the analyte), the Raman-active marker on the aptamer is brought into proximity of the SERS-active substrate and produces a strong Raman signal with a signature spectrum characteristic of the Raman-active marker. With the use of a different Raman-active marker for each aptamer (or aptamer set for a specific target), this assay can readily be adapted for multiplexing.

SUMMARY OF THE INVENTION

One embodiment of the invention is directed to a method of detecting a target molecule in a sample which comprises contacting said sample with one or more target-specific aptamers covalently or non-covalently attached to a SERS-active surface, said one or more aptamers (each) having a Raman-active marker covalently attached thereto, such that upon binding of said target to said one or more aptamers, said Raman-active marker is in sufficient proximity of the Raman-active surface to generate a detectable Raman signal. Hence, target-specific signal is detected upon complex formation because the Raman active marker has been brought into proximity of the SERS-active substrate. This detection scheme has many advantages over those known in the art. For example, it avoids the complexity of sandwich assays such as those used in ELISA format and it looks for an increase in signal rather than signal decrease often used in other types of assays.

The invention also provides target-specific aptamers with a covalently bound Raman-active marker at the 5' or 3' terminus of the aptamer, or alternatively within 1-10 bases of the terminus of the aptamer, or alternatively anywhere along the aptamer backbone, so long as binding of the analyte induces the aptamer to undergo a conformation change, to thereby bring the Raman-active marker into close proximity with the SERS-active surface. The aptamer can be attached via a thiol linkage, or by other convenient moiety, the marker can be incorporated via a modified oligonucleotide or other covalent or non-covalent linkage. In other embodiments, one or more oligonucleotides may be attached to the SERS active surface, which can be hybridized to the aptamer. In some embodiments, the aptamers of the invention are target-specific with a terminal thiol modification. In some embodiments, the Raman-active marker is covalently conjugated to the aptamers at predetermined locations along the aptamer backbone. In some embodiments, the marker is FAM, TAMRA, Cy3, Texas-Red (TR), Cy3.5, Rhodamine 6G, Cy5, or the like, or combination thereof.

Another aspect of the invention provides a composition of matter comprising a SERS-active surface covalently or coordinate covalently bound with a target-specific DNA aptamer having a Raman-active marker integrated into the DNA backbone at predetermined locations along its length, and, on binding of said aptamer to its target, said marker being sufficiently proximate to said SERS-active surface to produce a Raman signature spectrum for said marker upon excitation.

Another aspect of the invention relates to a surface enhanced Raman spectroscopy (SERS)-active reagent for detecting an analyte comprising: (a) one or more SERS-active surface; (b) unmodified or modified with one or more aptamer; and (c) one or more Raman-active marker. In some embodiments, the reagent comprises in (c) unmodified or modified with one or more Raman-active marker.

In certain embodiments, the SERS-active surface is selected from the group consisting of metals (including but not limited to silver, gold, Cu, certain other transition metals and titanium nitride) semiconductor substrates (including but not limited to titanium oxide, zinc oxide, zinc selenide) or semimetals (including but not limited to graphene and molybdenum disulfide). In certain embodiments, the SERS active surface may be a nanoparticle (NP) that is introduced into the biological samples, or the SERS active material may be a solid support into which NPs (SERS-active or inert) have or have not been embedded. The support material could be composed of materials including but not limited to: paper, cellulose, plastics including polystyrene, polyethylene and polydimethyl siloxane (PDMS). In some embodiments, these support materials are coated with one or several SERS-active materials. Another embodiment would be a patterned surface composed of one or several of those support materials coated with one or several SERS-active materials. In certain embodiments, the aptamer is functionalized.

In certain embodiments, the aptamer is functionalized 1) with thiol to bind to the SERS-active surface and 2) with Raman-active markers to enhance detection.

In certain embodiments, the aptamer is covalently or non-covalently attached to the SERS-active surface.

In certain embodiments, the SERS-active surface is unmodified with one or more aptamer.

In certain embodiments, the aptamer comprises a nucleotide sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, and 66.

In certain embodiments, the Raman-active marker comprises a dye or fluorescent marker.

In certain embodiments, the Raman-active marker is a fluorescent marker, and said fluorescent marker is selected from the group consisting of fluorescein (FAM), Carboxytetramethylrhodamine (TAMRA), Cy3, Texas-Red (TR), Cy3.5, Rhodamine 6G, Cy5, TRIT (tetramethyl rhodamine isothiol), NBD (7-nitrobenz-2-oxa-1,3-diazole), phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, quantum dots, carbon nanotubes, and fullerenes.

In certain embodiments, the Raman-active marker undergoes a conformational change upon binding of the analyte.

In certain embodiments, the aptamer undergoes a conformational change upon binding of the analyte.

In certain embodiments, the conformational changes of the aptamer upon binding of the analyte bring the Raman-active marker into close proximity to the surface of the SERS-active surface and leads to an enhancement in the Raman signal.

In certain embodiments, the Raman-active marker is covalently attached to the aptamer.

In certain embodiments, the analyte is selected from the group consisting of amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product, drugs of abuse, contaminant and gunshot residue.

Yet another aspect of the invention relates to a diagnostic kit comprising: a) at least one SERS-active reagent; said reagent comprising: (i) one or more SERS-active surface; (ii) unmodified or modified with one or more aptamer; and (iii) one or more Raman-active marker; b) a Raman-active marker control to show that the Raman-based detection system is working; c) at least one blood, serum, other fluid or tissues sample, or laboratory prepared positive control; and c) at least one blood, serum other fluid or tissues sample, or laboratory prepared negative control. In some embodiments, the reagent comprises in (iii) unmodified or modified with one or more Raman-active marker.

In certain embodiments, the kit may further comprise a sampling cartridge.

Another aspect of the invention relates to a detection system comprising; a) unmodified or modified with one or more SERS-active reagent; said reagent comprising: (i) one or more SERS-active surface; (ii) one or more aptamer; and (iii) one or more Raman-active marker; and b) a Raman detector or Raman instrument. In some embodiments, the reagent comprises in (iii) unmodified or modified with one or more Raman-active marker.

In certain embodiments, the Raman detector is portable.

In certain embodiments, the system further comprises a sample collection apparatus.

Another aspect of the invention relates to a method for determining the presence of one or more analyte in a biological sample, the method comprising: a) receiving a biological sample; b) contacting the biological sample to at least one SERS-active reagent comprising: (i) one or more SERS-active surface; (ii) unmodified or modified with one or more aptamer; and (iii) one or more Raman-active marker; c) allowing the analyte to come into contact with the aptamer; d) binding of the analyte by the aptamer, wherein said binding causes the aptamer to undergo a conformational change; e) irradiating the at least one SERS-active reagent bound to the one or more analyte; f) detecting the Raman signal to generate a Raman spectra; and g) comparing the Raman signal detected in (f) with a reference Raman signal of a control, wherein the presence of one or more analyte in the biological sample is determined when said Raman signal detected in (f) differs from said reference Raman signal. In certain embodiments of step (e), the SERS-active surface is bound to the aptamer, which recognizes the analyte. In certain embodiments of step (g), the presence of one or more analyte in the biological sample is determined when said Raman signal detected in (f) differs from the Raman signal in the absence of the target analyte. In some embodiments, the reagent comprises in (iii) unmodified or modified with one or more Raman-active marker.

Analogously, the invention relates to a method for determining the presence of one or more analyte in a biological sample, the method comprising: a) obtaining a biological sample; b) contacting the biological sample to at least one SERS-active reagent comprising: (i) unmodified or modified with one or more SERS-active surface; (ii) one or more aptamer; and (iii) one or more Raman-active marker; c) allowing the analyte to come into contact with the aptamer; d) binding of the analyte by the aptamer, wherein said binding causes the aptamer to undergo a conformational change; e) irradiating the at least one SERS-active reagent bound to the one or more analyte; f) detecting the Raman signal to generate a Raman spectra; and g) comparing the Raman signal detected in (f) with a reference Raman signal of a control, wherein the presence of one or more analyte in the biological sample is determined when said Raman signal detected in (f) differs from said reference Raman signal. In some embodiments, the reagent comprises in (iii) unmodified or modified with one or more Raman-active marker.

In certain embodiments, an increase in the Raman signal in the Raman spectra in (f) compared to control is correlated with the amount of the one or more analyte.

In certain embodiments, the conformational change of the aptamer upon binding of the analyte brings the Raman-active marker into close proximity to the surface of the SERS-active material.

In certain embodiments, the method may be used to detect 1, 2, 3, 4, 5, 6, 7, 8, 9, 10, or more analytes in a biological sample.

Another aspect of the invention relates to a method for diagnosing a disease or disorder in a subject comprising the steps of: a) receiving a biological sample from a subject; b) contacting the biological sample to at least one SERS-active reagent comprising: (i) one or more SERS-active surface; (ii) unmodified or modified with one or more aptamer; and (iii) one or more Raman-active marker; c) allowing binding of the analyte by at least one SERS reagent in the biological sample, wherein said binding causes a conformational change to the one or more aptamer(s) of the SERS reagent; d) irradiating the at least one SERS-active reagent bound to the one or more analyte; e) detecting the Raman signal of the at least one SERS-active reagent; and f) comparing the Raman signal of said at least one SERS-active reagent detected in (e) with a reference Raman signal of said at least one SERS-active reagent detected in a biological sample received from a control subject (healthy subject), wherein said disease is diagnosed when said Raman signal detected in (e) differs from said reference Raman signal in position and/or intensity of the Raman-sensitive marker peak. In some embodiments, the reagent comprises in (iii) unmodified or modified with one or more Raman-active marker.

Analogously, the invention relates to a method for diagnosing a disease or disorder in a subject comprising the steps of: a) obtaining a biological sample from a subject; b) contacting the biological sample to at least one SERS-active reagent comprising: (i) one or more SERS-active surface; (ii) unmodified or modified with one or more aptamer; and (iii) one or more Raman-active marker; c) allowing binding of the one or more analyte by at least one SERS reagent in the biological sample, wherein said binding causes a conformational change to the one or more aptamer of the SERS reagent; d) irradiating the at least one SERS-active reagent bound to the one or more analyte; e) detecting the Raman signal of the at least one SERS-active reagent; and f) comparing the Raman signal of said at least one SERS-active reagent detected in (e) with a reference Raman signal of said at least one SERS-active reagent detected in a biological sample received from a control subject (healthy subject), wherein said disease is diagnosed when said Raman signal detected in (e) differs from said reference Raman signal in position and/or intensity of the Raman-sensitive marker peak. In some embodiments, the reagent comprises in (iii) unmodified or modified with one or more Raman-active marker.

Alternatively, the invention relates to a method for diagnosing a disease or disorder in a subject, comprising: a) receiving a Raman signal measured in a biological sample of a subject; b) receiving a reference Raman signal measured in a biological sample of a control subject; and c) comparing the Raman signal of (a) with the reference Raman signal of (b), wherein said disease is diagnosed when said Raman signal in (a) differs in location and/or intensity from said reference Raman signal in (b).

In certain embodiments, the disease or disorder is selected from the group consisting of an infectious disease, proliferative disease, neurodegenerative disease, cancer, psychological disease, metabolic disease, autoimmune disease, sexually transmitted disease, gastro-intestinal disease, pulmonary disease, cardiovascular disease, stress- and fatigue-related disorder, fungal disease, pathogenic disease, and obesity-related disorder.

The present invention is directed to reagents for and methods of detecting analytes bound by functionalized aptamers using surface-enhanced Raman scattering (SERS). The system is composed of three parts: a SERS-active surface or nanoparticle (henceforth referred to as SERS-active surface), an aptamer, and a Raman-active marker attached to the aptamer. The functionalized aptamer is covalently or non-covalently attached to the SERS-active surface. When this complex is contacted with a sample containing the aptamer binding target (i.e., the analyte), the Raman-active marker on the aptamer is brought into proximity of the SERS-active substrate and resulting in the observation of a strong Raman signal with a signature characteristic(s) of the Raman-active marker. With the use of a different Raman-active marker for each aptamer (or aptamer set for a specific target), this assay can readily be adapted for multiplexing.

Another aspect of the invention relates to a surface enhanced Raman spectroscopy (SERS)-active reagent for detecting one or more analyte in a species of *Borrelia* comprising: (a) one or more SERS-active surface; (b) one or more aptamer directed to one or more analyte found in a species of *Borrelia*; and (c) one or more Raman-active marker.

In certain embodiments, the SERS-active surface is selected from the group consisting of metals (including but not limited to silver, gold, Cu, certain other transition metals and titanium nitride) semiconductor substrates (including but not limited to titanium oxide, zinc oxide, zinc selenide) or semimetals (including but not limited to graphene and molybdenum disulfide).

In certain embodiments, the aptamer is functionalized.

In certain embodiments, the aptamer is functionalized 1) to bind the aptamer to the SERS-active surface and 2) with Raman-active markers to enhance detection.

In certain embodiments, the aptamer is covalently or non-covalently attached to the SERS-active surface.

In certain embodiments, the aptamer comprises a nucleotide sequence which is at least 80% identical to the nucleotide sequences selected from the group consisting of SEQ ID NOs: 67-84.

In certain embodiments, the Raman-active marker comprises a dye, azide, alkyne, quantum dot, carbon nanotube, or fluorescent marker.

In certain embodiments, the Raman-active marker is a fluorescent marker, and said fluorescent marker is selected from the group consisting of azides, alkynes, fluorescein (FAM), Carboxytetramethylrhodamine (TAMRA), Cy3, Texas-Red (TR), Cy3.5, Rhodamine 6G, Cy5, TRIT (tetramethyl rhodamine isothiol), NBD (7-nitrobenz-2-oxa-1,3-diazole), phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, quantum dots, carbon nanotubes, and fullerenes.

In certain embodiments, the aptamer conjugated to the Raman-active marker undergoes reorganization upon binding of the analyte.

In certain embodiments, the aptamer conjugated to the Raman-active marker undergoes a conformational change upon binding of the analyte.

In certain embodiments, the conformational change of the aptamer upon binding of the analyte brings the Raman-active marker into close proximity to the surface of the SERS-active surface and causes an enhancement in the Raman signal.

In certain embodiments, the Raman-active marker is covalently attached to the aptamer. In certain embodiments, the analyte is selected from the group consisting of surface protein, amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product, drugs of abuse, contaminant, and gun shot residue.

In certain embodiments, the species of *Borrelia* is selected from *Borrelia afzelii*, *Borrelia americana*, *Borrelia andersonii*, *Borrelia anserina*, *Borrelia baltazardii*, *Borrelia bavariensis*, *Borrelia bissettii*, *Borrelia brasiliensis*, *Borrelia burgdorferi*, *Borrelia californiensis*, *Borrelia carolinensis*, *Borrelia caucasica*, *Borrelia coriaceae*, *Borrelia cro-*

*cidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mazzottii, Borrelia merionesi, Borrelia microti, Borrelia miyamotoi, Borrelia parkeri, Borrelia persica, Borrelia recurrentis, Borrelia sinica, Borrelia spielmanii, Borrelia tanukii, Borrelia texasensis, Borrelia theileri, Borrelia tillae, Borrelia turcica, Borrelia turdi, Borrelia turicatae, Borrelia valaisiana, Borrelia venezuelensis, Borrelia vincentii, Borrelia burgdorferi* B31, *Borrelia burgdorferi* N40, *Borrelia burgdorferi* JD1, or *Borrelia burgdorferi* 297.

Another aspect of the invention relates to a diagnostic kit comprising: a) at least one SERS-active reagent; said reagent comprising: (i) one or more SERS-active surface; (ii) one or more aptamer directed to one or more analyte found in a species of *Borrelia*; and (iii) one or more Raman-active marker; b) at least one positive control; and c) at least one negative control.

Another aspect of the invention relates to a detection system comprising: a) one or more SERS-active reagent; said reagent comprising: (i) one or more SERS-active surface; (ii) one or more aptamer directed to one or more analyte found in a species of *Borrelia*; and (iii) one or more Raman-active marker; and b) a Raman detector.

In certain embodiments, the Raman detector is portable or not portable.

In certain embodiments, the system further comprises a sample collection apparatus.

Another aspect of the invention relates to a method for determining the presence of one or more analyte in a biological sample, the method comprising: a) receiving a biological sample; b) contacting the biological sample to at least one SERS-active reagent comprising: (i) one or more SERS-active surface; (ii) one or more aptamer directed to one or more analyte found in a species of *Borrelia*; and (iii) one or more Raman-active marker; c) allowing the analyte to come into contact with the aptamer; d) binding of the analyte by the aptamer, wherein said binding causes the one or more aptamer(s) to undergo a conformational change; e) irradiating the at least one SERS-active reagent bound to the one or more aptamer; f) detecting the Raman signal to generate a Raman spectrum; and g) comparing the Raman signal detected in (f) with a reference Raman signal of a control, wherein the presence of one or more analyte in the biological sample is determined when said Raman signal detected in (f) differs from said reference Raman signal in position and/or intensity of the peak associated with Raman-sensitive marker. The methods of the present invention allows for the direct detection of *Borrelia* and/or the detection of anti-*Borrelia* antibodies.

Analogously, the invention relates to a method for determining the presence of one or more analyte in a biological sample, the method comprising: a) obtaining a biological sample; b) contacting the biological sample to at least one SERS-active reagent comprising: (i) one or more SERS-active surface; (ii) one or more aptamer directed to one or more analyte found in a species of *Borrelia*; and (iii) one or more Raman-active marker; c) allowing the analyte to come into contact with the aptamer; d) binding of the analyte by the aptamer, wherein said binding causes the one or more aptamer to undergo a conformational change; e) irradiating the at least one SERS-active reagent bound to the one or more analyte; f) detecting the Raman signal to generate a Raman spectra; and g) comparing the Raman signal detected in (f) with a reference Raman signal of a control, wherein the presence of one or more analyte in the biological sample is determined when said Raman signal detected in (f) differs from said reference Raman signal. The methods of the present invention allows for the direct detection of *Borrelia*, as opposed to the detection of anti-*Borrelia* antibodies.

In certain embodiments, an increase in the Raman signal in the Raman spectra in (f) compared to control is correlated with the amount of the one or more analyte.

In certain embodiments, the conformational change of the aptamer upon binding of the analyte brings the Raman-active marker into close proximity to the surface of the SERS-active nanoparticle.

In certain embodiments, the method may be used to detect 1, 2, 3, 4, 5, 6, 7, 8, 9, 10, or more analytes in a biological sample.

Another aspect of the invention relates to a method for diagnosing a Lyme disease in a subject comprising the steps of: a) receiving a biological sample from a subject; b) contacting the biological sample to at least one SERS-active reagent comprising: (i) one or more SERS-active surface(s); (ii) one or more aptamer directed to one or more analyte found in a species of *Borrelia*; and (iii) one or more Raman-active marker; c) allowing binding of the at least one SERS reagent by one or more analyte in the biological sample, wherein said binding causes a conformational change to the one or more aptamers of the SERS reagent; d) irradiating the at least one SERS-active reagent bound to the one or more analyte; e) detecting the Raman signal of the at least one SERS-active reagent; and f) comparing the Raman signal of said at least one SERS-active reagent detected in (e) with a reference Raman signal of said at least one SERS-active reagent detected in a biological sample received from a control subject (healthy subject), wherein said Lyme disease is diagnosed when said Raman signal detected in (e) differs from said reference Raman signal. In certain embodiments of step (d), the SERS-active reagent is bound to the aptamer, which recognizes the analyte. In certain embodiments of step (f), said Raman signal detected in (e) differs from the Raman signal in the absence of the target analyte.

Analogously, the invention relates to a method for diagnosing a Lyme disease in a subject comprising the steps of: a) obtaining a biological sample from a subject; b) contacting the biological sample to at least one SERS-active reagent comprising: (i) one or more SERS-active surface; (ii) one or more aptamer directed to one or more analyte found in a species of *Borrelia*; and (iii) one or more Raman-active marker; c) allowing binding of the at least one SERS reagent by one or more analyte in the biological sample, wherein said binding causes a conformational change to the one or more aptamers of the SERS reagent; d) irradiating the at least one SERS-active reagent bound to the one or more aptamer; e) detecting the Raman signal of the at least one SERS-active reagent; and f) comparing the Raman signal of said at least one SERS-active reagent detected in (e) with a reference Raman signal of said at least one SERS-active reagent detected in a biological sample received from a negative control subject (healthy subject), pooled samples from numerous negative control subjects, or a laboratory prepared negative control sample wherein said Lyme disease is diagnosed when said Raman signal detected in (e) differs from said reference Raman signal.

Alternatively, the invention relates to a method for diagnosing Lyme disease in a subject, comprising: a) receiving a Raman signal measured in a biological sample of a subject; b) receiving a reference Raman signal measured in a biological sample of a control subject; and c) comparing the Raman signal of (a) with the reference Raman signal of (b), wherein said Lyme disease is diagnosed when said Raman signal in (a) differs in position and/or intensity from said reference Raman signal in (b).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

A. Definitions

Figure 1:
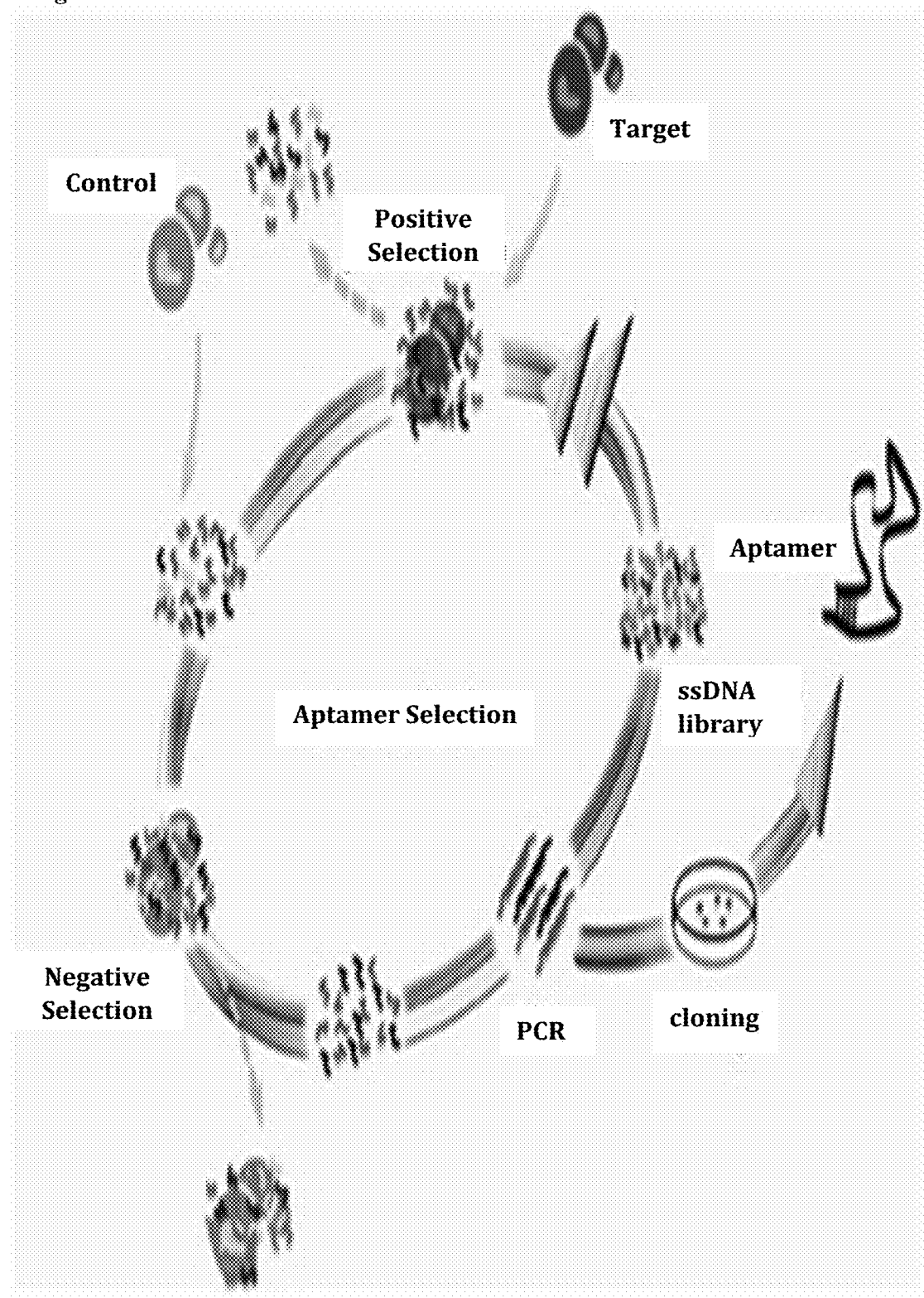
FIG. 1 depicts a schematic figure showing the in vitro evolution of aptamers using SELEX. Typically 8-12 rounds of selection are used to generate tight binding, high specificity aptamers.
Figure 2A:
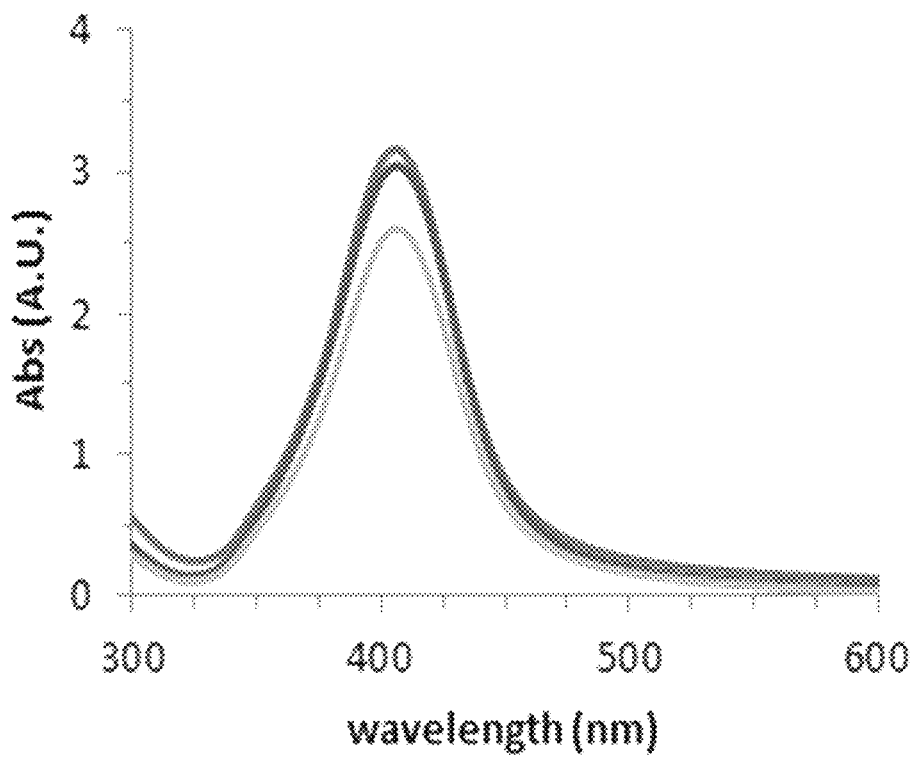
FIG. 2 contains six panels. Panel A depicts a comparison of absorption spectra of silver NPs produced using the microwave-based synthetic method. The plasmon absorption maximum at 401 nm, and a FWHM of 60 nm are maintained by the Ag NPs over a three week period. Shown are the absorption spectra of NPs on the day they were synthesized (blue), and the same NPs three weeks after synthesis (red), and NPs stored in the reaction mixture which were centrifuged three weeks after synthesis (green), demonstrating the ability of the NPs to maintain the observed spectral characteristics was not dependent on the method of purification. Panel B depicts a comparison of Raman spectra of 200 μM solutions of mercaptophenol (MCP) in the presence (blue) and absence (red) of Ag NPs. The asterisk indicates the spectral contribution of the silicon substrate on which the sample was dried. Panel C depicts absorption spectra of dithiol terminated DNA-modified Ag NPs upon addition of NaCl. Addition of 25 mM NaCl resulted in a decrease in absorption intensity that achieved a steady absorption after 15 min. Increasing the NaCl concentration to 50 mM resulted in further decrease in the intensity of the plasmon absorption. Addition of a third aliquot resulted in nearly complete loss of the plasmon absorption immediately after addition of the aliquot. Panels D and E depict spectral interrogation of the surface modification of Ag NPs with a dithiol-modified DNA. Panel D shows a representative spectral analysis of DNA-modified Ag NP plasmon absorption of NPs modified with DNA in the absence of a reducing agent. The spectra were recorded to follow the effect on the plasmon absorption of the addition 0 to 100 mM sodium chloride in 25 mM increments. Panel E shows a comparison of decrease in plasmon absorption intensity with addition of sodium chloride to Ag NPs modified with dithiol-terminated DNA. The change in absorption of the plasmon at 403 nm is shown as a fraction of the initial plasmon absorption intensity. Spectra were collected until the plasmon absorption intensity dropped below 50% of the initial intensity. Panel F depicts emission spectra of 5'-FAM, 3'-dithiol modified DNA after DTT treatment. FAM emission spectra resulting from DTT treatment of Ag NPs treated with DNA in the presence of TCEP reduced-(red, bottom) and disulfide DNA in the absence of reducing agent (blue, top).
Figure 2B:
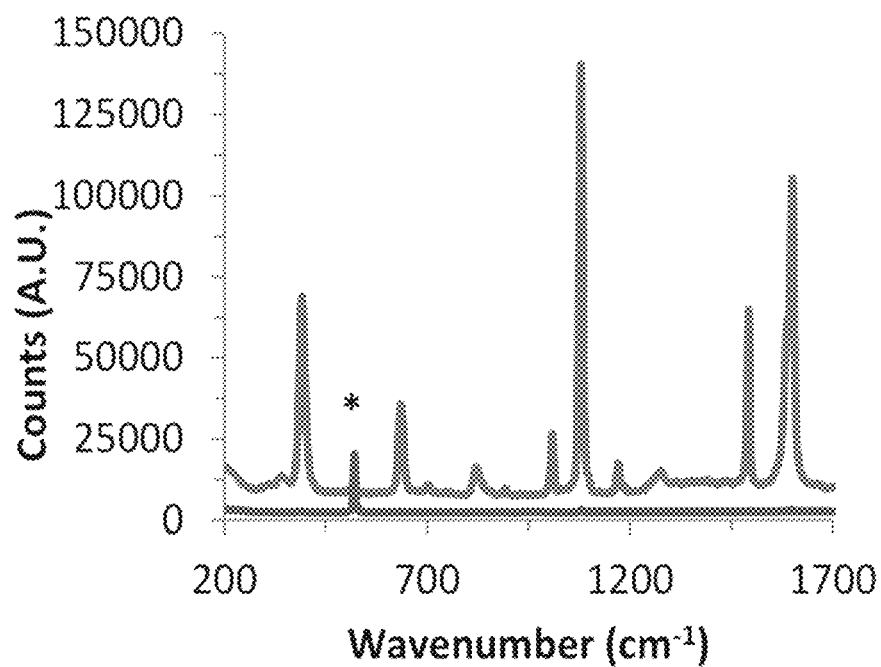
Figure 2C:
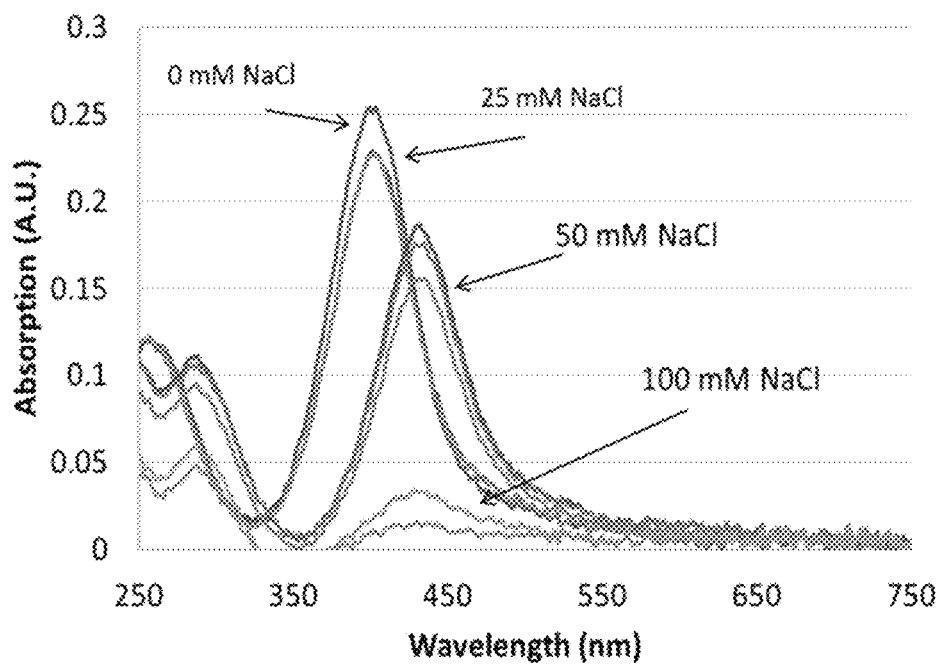
Figure 2D:
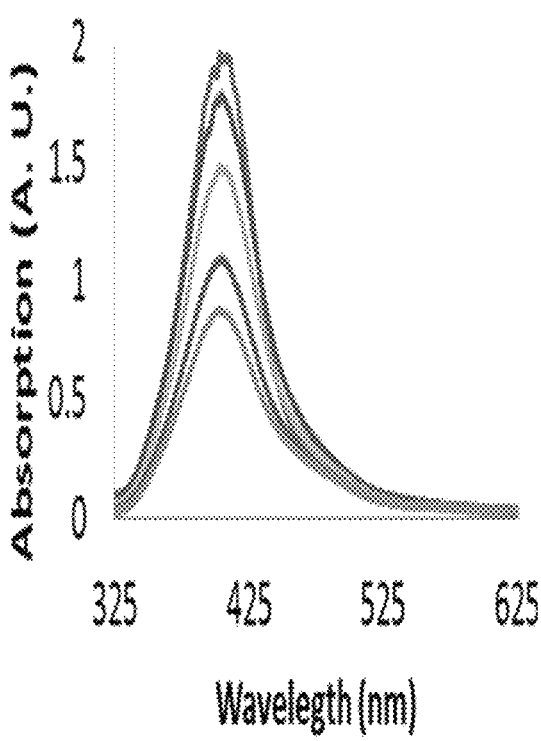
Figure 2E:
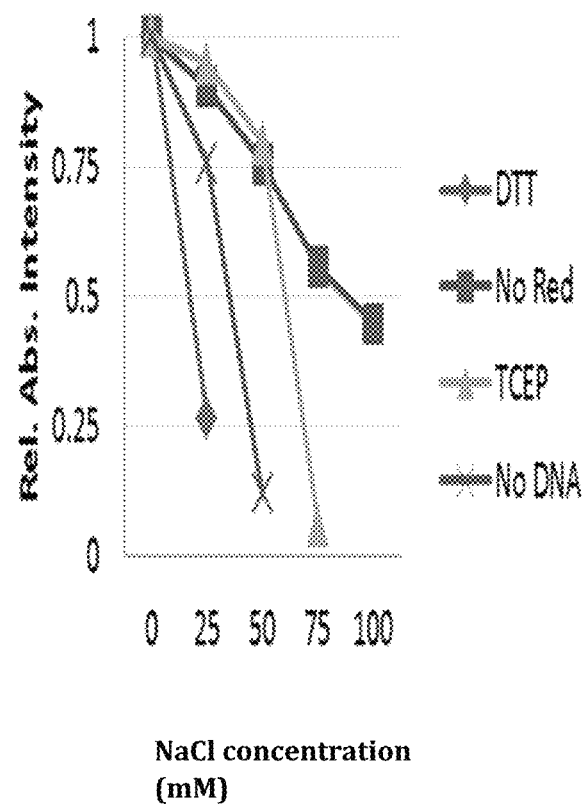
Figure 2F:
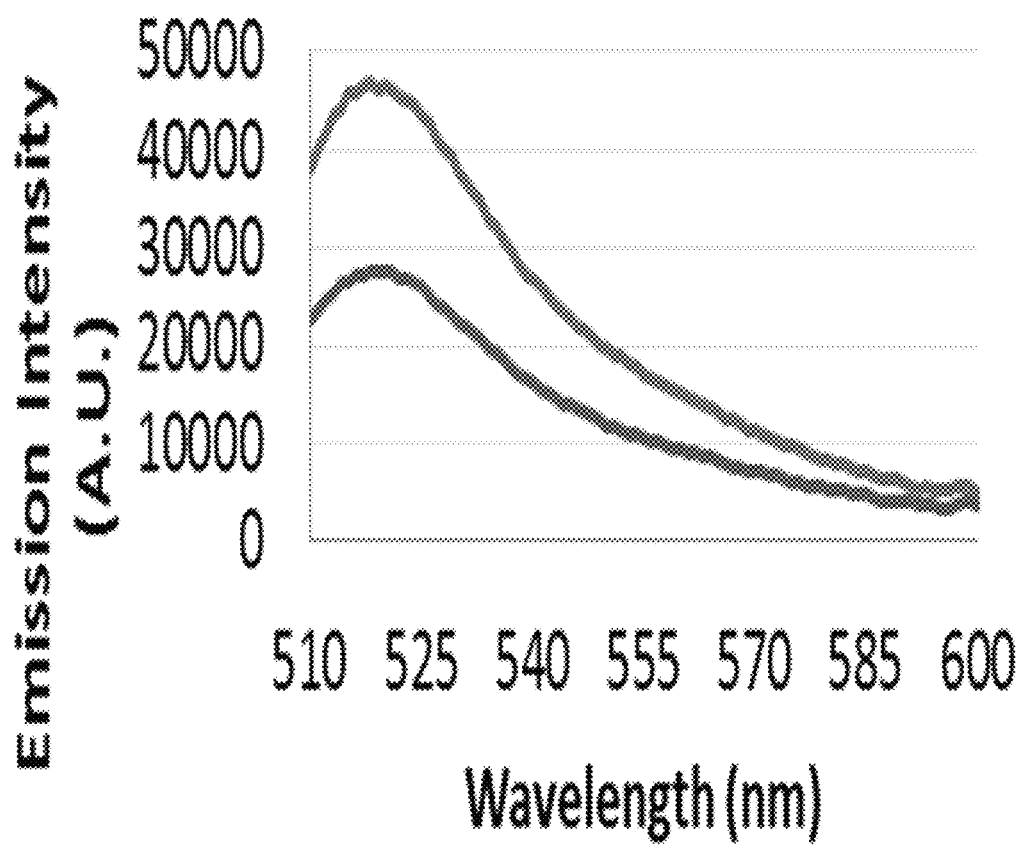
Figure 3A:
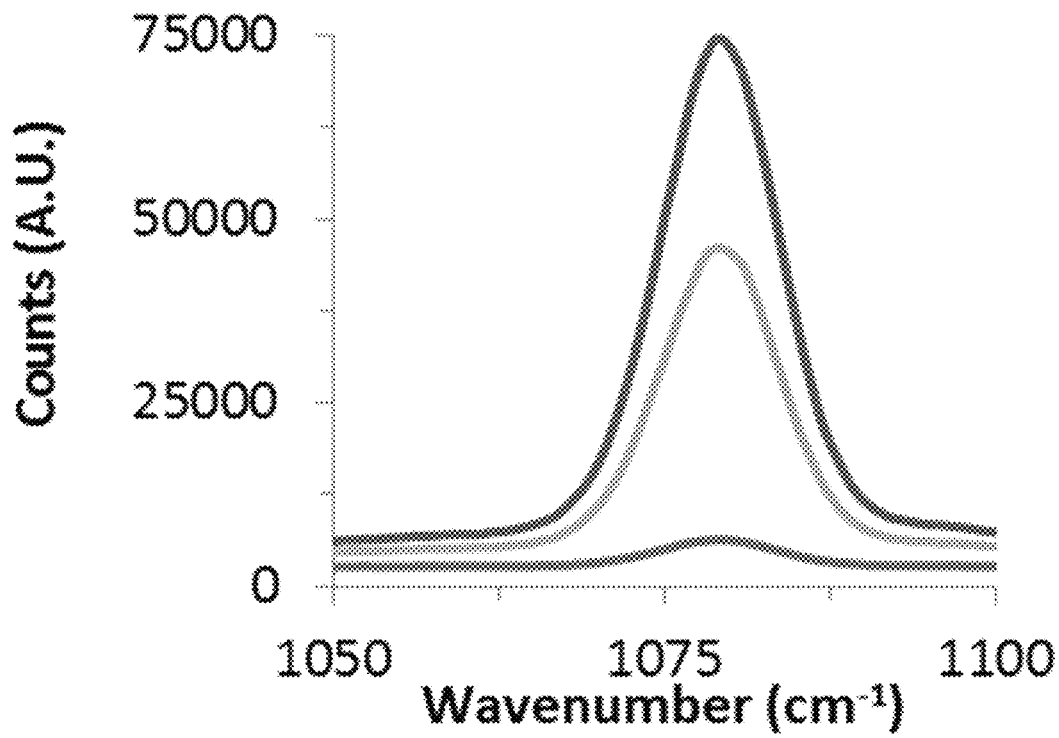
FIG. 3 contains six panels. Panel A depicts comparison of Raman spectra of 200 μM aqueous solutions of mercaptophenol (MCP) in the presence of 100 μM solutions of potassium nitrate (red, top), or sodium chloride (green), and in the absence of salt (blue, bottom). Panel B depicts comparison of the efficacy of salt additives on increasing Raman signal intensity. Raman spectra of AgNP surface modified with 5'-FAM dithiolated DNA reveal the addition of $KNO_3$ (green) produce more intense spectral features than in the presence of NaCl (red) or in the absence of added salt (blue) in producing the most intense spectral features. The DNA modification was performed in the presence of 50 mM NaCl. Panel C depicts a comparison of Raman spectra of Ag NPs modified with mixed monolayer composed of mercaptophenol and FAM-terminated DNA. Spectra shown, from bottom to top, are of Ag NPs with a monolayer of 4 μM mercaptophenol and mixed monolayers of FAM-modified DNA with concentrations of MCP ranging from 4 mM to 4 μM decreasing by an order of magnitude in each spectrum. Panel D depicts a comparison of Raman spectra of Ag NPs modified with mercaptophenol (MCP; bottom), FAM-terminated DNA (middle) and a mixed monolayer of FAM-terminated DNA with 4 mM MCP (top). All spectra offset for clarity; data collected with 632.8 nm incident light. The color of the arrow matches the source of the spectral feature; red arrows indicate contributions from MCP, and black arrows indicate contributions from FAM-terminated DNA. Panel E depicts a comparison of Raman spectra of Ag NPs modified with mercaptophenol (MCP; bottom), FAM-terminated DNA (middle) and a mixed monolayer of FAM-terminated DNA with 4 mM MCP (top) collected with 785 nm incident light. Arrows indicate spectral features derived from the components of the mixed monolayer. The features at 305 $cm^{-1}$, 714 $cm^{-1}$ and 1050 $cm^{-1}$ are derived from the FAM dye found at the 5'-terminus of the dithiol-modified DNA, whereas the features at 393 $cm^{-1}$, 636 $cm^{-1}$, 1010 $cm^{-1}$, 1080 $cm^{-1}$ and 1175 $cm^{-1}$ are contributions from the MCP monolayer. Panel F depicts a comparison of effect of concentration of MCP and MCH on spectral intensities of MCP and FAM on mixed monolayer Ag NPs. Shown are the spectral intensities observed of the FAM-derived feature (1050 $cm^{-1}$; blue and green) and MCP derived feature (1076 $cm^{-1}$; red and purple) at two concentrations of MCP. The spectral intensity of the two components of the mixed monolayer collected with 40 μM MCP (blue and red), and 4 μM MCP (green and purple).
Figure 3B:
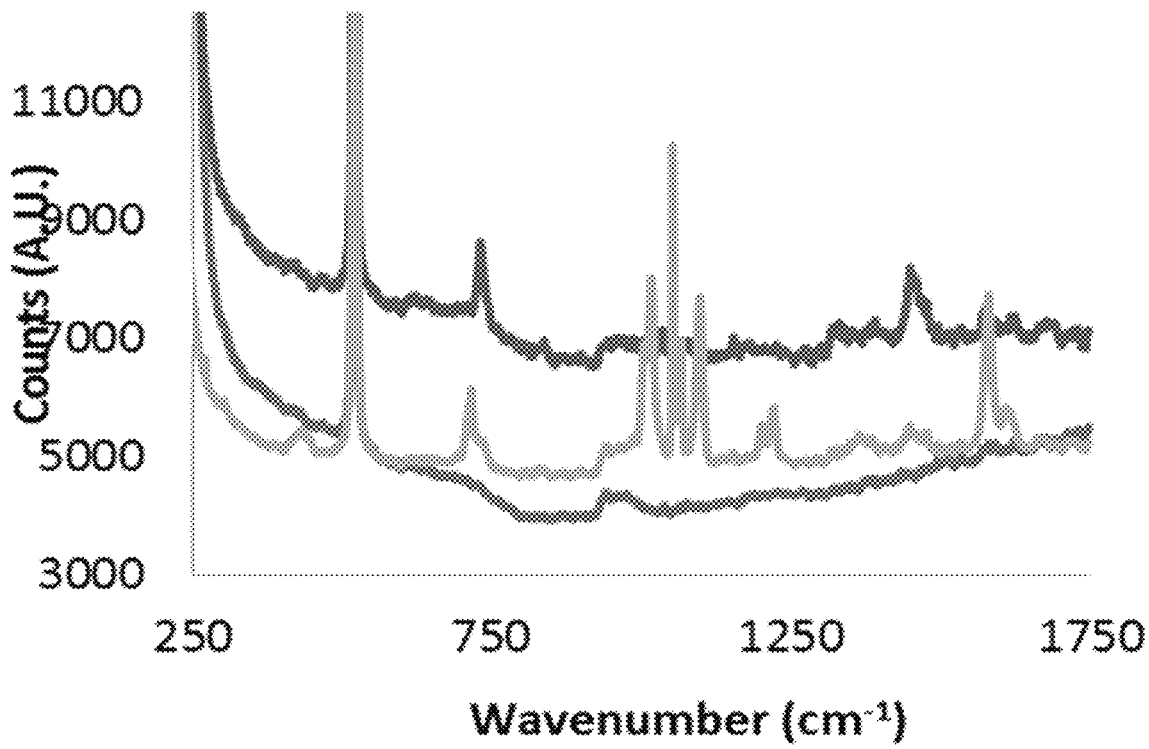
Figure 3C:
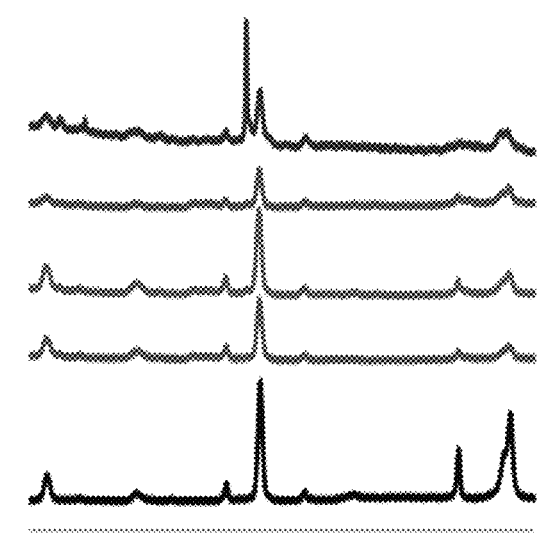
Figure 3D:
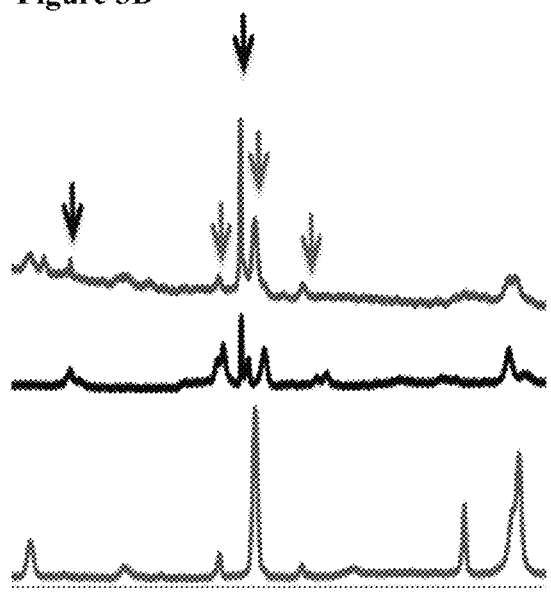
Figure 3E:
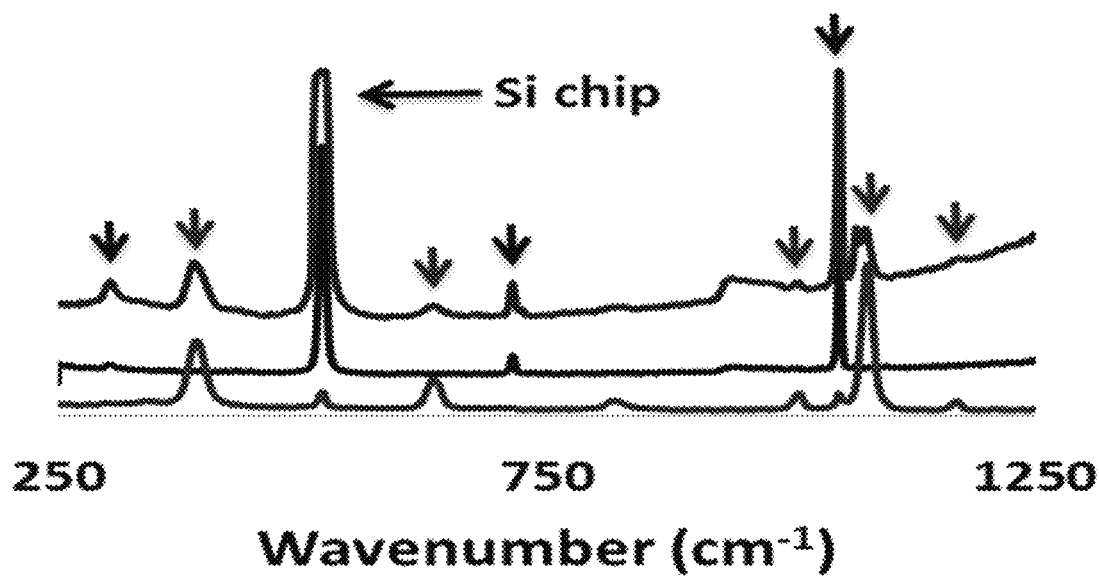
Figure 3F:
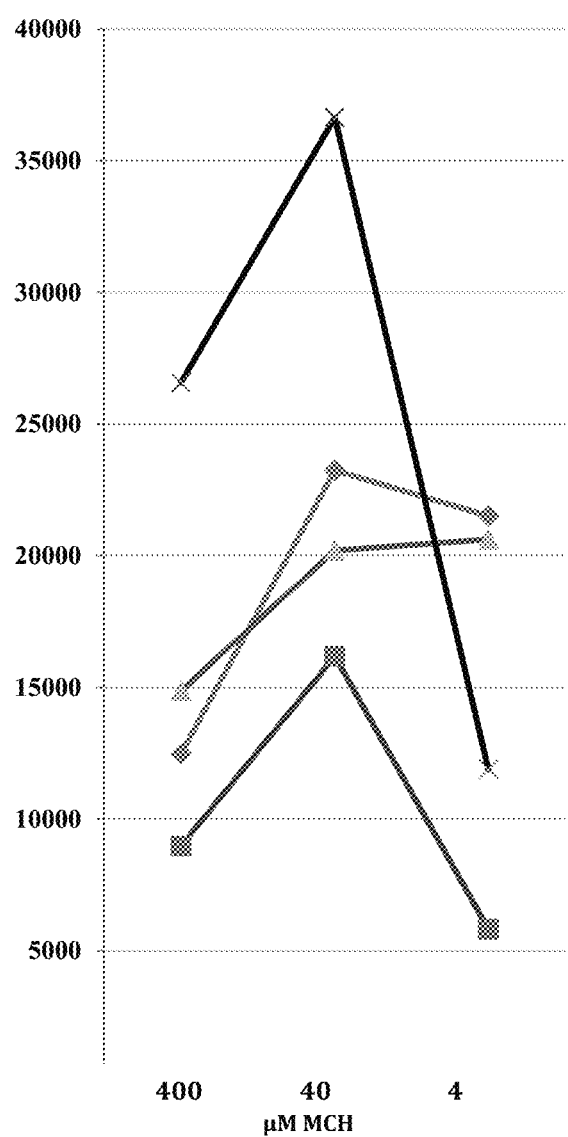

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

B. Nanoparticles and Other SERS Active Substrate Materials

SERS-active nanoparticles are used to provide the Raman-active surface of the invention and are known in the art. Other SERS-active material-coated surfaces, metal-coated surfaces, or surfaces with embedded SERS-active nanoparticles are contemplated by the invention. SERS-active nanoparticles include, but are not limited to, those described in U.S. Patent Appln. Pub. No. 2004/0134997. For example, silver (Ag) nanoparticles can be prepared using a microwave-based reduction of $AgNO_3$ or by any number of other methods known to those of skill in the art. Silver and gold nanoparticles are also known and used and can be obtained commercially or synthetically and adapted for use in the present methods. In addition to nanoparticles other SERS active substrates can be used including, but not limited to: core shell, hollow or Si beads coated with metals for Raman activity, or other SERS active substrates composed of metals, semiconductors or, semi-metals on appropriate supports, or polymeric surfaces coated with SERS-active materials; these materials may or may not have NPs embedded. Wang, W.; et al., *Appl. Phys. Lett.* 106, 2015, 211604.

In certain embodiments, the SERS active NP may be free and introduced into the biological samples, or the SERS active material may be a solid support into which NPs (SERS-active or inert) have been embedded. The support material could be composed of materials including but not limited to: paper, cellulose, plastics including polystyrene, polyethylene and polydimenthyl siloxane (PDMS) or other polymeric materials. In some embodiments, these support materials are coated with one or several SERS-active materials. Another embodiment would be a patterned surface composed of one or several of those support materials coated with one or several SERS-active materials (Wang, W.; et al. *Appl. Phys. Lett.* 106, 2015, 211604)

If aptamers are attached to the SERS active substrate, aptamers can be bound can be bound to the SERS-active surface either covalently or non-covalently. The DNA aptamer may be modified with the thiol. For covalent, dative or coordinate covalent attachment, the surface or SERS-active substrates can be modified to contain various reactive groups suitable for attaching DNA or RNA aptamers or oligonucleotides, typically thiols but any groups known in the art can be used. For example, a capping reagent such as dihydrolipoic acid can be covalently attached to the Raman-active surface and amine-terminated DNA aptamer can be covalently linked to the nanoparticle using standard amine to carboxylic acid conjugation with EDC (1-ethyl-3-(3-dimethylaminopropyl)carbodiimide). For non-covalent aptamer attachment, a barcode DNA, universal primer or other binding specific sequence of DNA (or RNA), i.e., a capture oligo, can be attached to the nanoparticles or SERS-active surfaces. Such capture oligos are hybridized with target-specific aptamers which have the complementary sequence of the capture oligo (typically at a significant distance or near the opposite end from the Raman active marker).

C. Aptamers

Aptamers are single-stranded nucleic acid (DNA or RNA) molecules, typically but not always, under 100 bases in length, which have the ability to bind to other molecules with high affinity and specificity. Aptamers can be generated, for example, using an in vitro evolutionary process using random oligonucleotide pools by a process called Systematic Evolution of Ligands by EXponential enrichment (SELEX; FIG. 1). The SELEX process is controlled by the ability of these small oligonucleotides to fold into unique three dimensional structures that can interact with a specific target with high specificity and affinity. Aptamers can be been generated against a wide variety of targets, including: metal ions,[1] small molecules such as organic dyes[2] and amino acids,[3] medically relevant molecules such as antibiotics[4] and peptides,[5] and biologically relevant molecules such as proteins,[6,7] whole cells, viruses and virus-infected cells,[8] and bacteria.[9,10] Once the sequences for a particular aptamer or aptamer set is known, the aptamers can readily be synthesized using standard techniques known in the art for oligonucleotides or via synthetic or recombinant DNA techniques. Aptamers that bind oxytocin, vasopressin, other hormones, infectious disease agents, and disease marker proteins are of particular interest.

In addition, the aptamers may bind illicit drugs, such as but not limited to, cannabinoids/*Cannabis*/Marijuana (Δ9-Tetrahydrocannabinol, THC), synthetic cannabinoids, Carisoprodol (and Meprobamate), Cocaine (Methylbenzoylecgonine), Dextromethorphan, Diphenhydramine, Gamma-Hydroxybutyrate (GHB, GBL, and 1,4-BD), Ketamine, Lysergic acid diethylamide (LSD), buprenorphine (subutex), Methadone, Methamphetamine, Amphetamine, Methylenedioxymethamphetamine (MDMA, Ecstasy), barbiturates, benzodiazepines, opiates (Oxycodone, propoxyphene, Morphine and Heroin), or Phencyclidine (PCP).

The aptamers of the present invention are useful for diagnostic and prognostic applications such as detecting persistent infectious disease, proliferative diseases, neurodegenerative diseases, cancers, psychological diseases, metabolic diseases, autoimmune diseases, sexually transmitted diseases, gastro-intestinal diseases, pulmonary diseases, cardiovascular diseases, stress- and fatigue-related disorders, fungal diseases, pathogenic diseases, obesity-related disorders, or biomarkers regarding same. Viral infectious diseases including human papilloma virus (HPV), hepatitis A Virus (HAV), hepatitis B Virus (HBV), hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, influenza virus, Hepatitis A and B, FIV, lentiviruses, pestiviruses, West Nile Virus, measles, smallpox, cowpox, ebola, coronavirus, retrovirus, herpesvirus, potato S virus, simian Virus 40 (SV40), Mouse Mammary Tumor Virus (MMTV) promoter, Moloney virus, ALV, Cytomegalovirus (CMV), Epstein Barr Virus (EBV), or Rous Sarcoma Virus (RSV). The aptamers of the present invention may detect antigens, antibodies, or other analytes associated with pathogens such as various parasites, like malaria. In addition, bacterial, fungal and other pathogenic diseases are included, such as *Aspergillus, Brugia, Candida, Chikungunya, Chlamydia, Coccidia, Cryptococcus, Dengue, Dirofilaria, Gonococcus, Histoplasma, Leishmania, Mycobacterium, Mycoplasma, Paramecium, Pertussis, Plasmodium, Pneumococcus, Pneumocystis, P. vivax* in *Anopheles* mosquito vectors, *Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis,* Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus* equi, *Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Clostridium difficile, Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, yellow fever in *Aedes* mosquitoes, and multidrug-resistant tuberculosis; helminths, such as *Schistosoma* and *Taenia*; and protozoa, such as *Leishmania* (e.g., *L. mexicana*) in sand flies, *Plasmodium*, Chagas disease in assassin bugs.

Bacterial pathogens include, but are not limited to, such as bacterial pathogenic gram-positive cocci, which include but are not limited to: pneumococci; staphylococci; and streptococci. Pathogenic gram-negative cocci include: meningococci; and gonococci. Pathogenic enteric gram-negative bacilli include: enterobacteriaceae; *pseudomonas*, acinetobacteria and eikenella; melioidosis; *salmonella*; shigellosis; *hemophilus*; chancroid; brucellosis; tularemia; *yersinia (pasteurella); Streptobacillus moniliformis* and spirilum; *Listeria monocytogenes*; erysipelothrix rhusiopathiae; diphtheria; cholera; anthrax; and donovanosis (*Granuloma inguinale*). Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of *mycoplasma* and chlamydial infections include: *Mycoplasma pneumoniae; Lymphogranuloma venereum*; psittacosis; and perinatal chlamydial infections. Pathogenic protozoans and helminths and infections eukaryotes thereby include: amebiasis; malaria; leishmaniasis; trypanosomiasis; toxoplasmosis; *Pneumocystis carinii*; giardiasis; trichinosis; filariasis; schistosomiasis; nematodes; trematodes or flukes; and cestode (tapeworm) infections.

The aptamers of the present invention are useful for diagnostic and prognostic applications such as detecting persistent infectious disease. In certain embodiments, the aptamers may detect infections caused by species in the family of *Borrelia*, such as *B. burgdorferi* infections, in humans using human blood, serum or plasma, taken from a finger stick or standard blood draw. In addition, the aptamers may detect Lyme and other tick-borne pathogens, such as: *Babesia, Ehrlichia, Anaplasma, Bartonella*, and other emerging tick borne pathogens such as *Borrelia miyamotoi*, spotted fevers, and Powassan virus. The aptamer may be used to detect *Borrelia afzelii, Borrelia americana, Borrelia andersonii, Borrelia anserina, Borrelia baltazardii, Borrelia bavariensis, Borrelia bissettii, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mazzottii, Borrelia merionesi, Borrelia microti, Borrelia miyamotoi, Borrelia parkeri, Borrelia persica, Borrelia recurrentis, Borrelia sinica, Borrelia spielmanii, Borrelia tanukii, Borrelia texasensis, Borrelia theileri, Borrelia tillae, Borrelia turcica, Borrelia turdi, Borrelia turicatae, Borrelia valaisiana, Borrelia venezuelensis, Borrelia vincentii, Borrelia burgdorferi* B31, *Borrelia burgdorferi* N40, *Borrelia burgdorferi* JD1, or *Borrelia burgdorferi* 297. The *Borrelia* species may be found in *Ixodes scapularis* ticks.

"*Babesia*" refers to infectious protozoan species of the *Babesia* family, including but not limited to, *Babesia bigemina, Babesia bovis, Babesia canis, Babesia cati, Babesia divergens, Babesia duncani, Babesia felis, Babesia gibsoni, Babesia herpailuri, Babesia jakimovi, Babesia major, Babesia microti, Babesia ovate*, or *Babesia pantherae*. "*Ehrlichia*" refers to the infections pathogenic species of the *Ehrlichia* family, including but not limited to, *Ehrlichia chaffeensis, Ehrlichia muris, Ehrlichia ewingii, Ehrlichia ruminantium*, or *Ehrlichia canis*. "*Anaplasma*" refers to the infections pathogenic species of the *Anaplasma* family, including but not limited to, *Anaplasma phagocytophilum, Anaplasma marginale, Anaplasma centrale, Anaplasma mesaeterum, Anaplasma ovis*, or *Anaplasma* platys. "*Bartonella*" refers to the infections pathogenic species of the *Bartonella* family, including but not limited to *Bartonella henselae, Bartonella quintana, Bartonella bacilliformis, Bartonella elizabethae*, or *Bartonella clarridgeiae*.

On the basis of their target-recognition capability, selectivity and high affinity binding, aptamers have been likened to antibodies. However, aptamers, by their unique features, have more flexibility in their development and range of applications. Specifically, the time needed for the generation of aptamers by the SELEX process is comparatively short. In addition, aptamers can be chemically synthesized, which permits the biochemical manipulation required to incorporate various functional groups and specific moieties such as biotin, carboxyl, amino and thiol groups, most of which do not affect the recognition of the target by the aptamer. Aptamers are amenable to in vitro evolution, where increased pressure can be applied during the selection process, potentially increasing the affinity or selectivity of the aptamers for their target.

For example, aptamers are selected from a pool of $10^{14}$ to $10^{15}$ random DNA or RNA sequence aptamers (purchased as a pool from a commercial source that produces synthetic oligonucleotides), and the sequence-specific aptamers are enriched using the SELEX process. SELEX involves exposure of the DNA or RNA aptamer pool to a target, typically on solid support, as well as "negative" targets (i.e., other parts of the process, such as the plastic used in the process or the solid support in the absence of the target) to ensure the pool is not enriched for "negative" targets. The aptamers interact with and are bound to the target, and non-bound aptamers are washed away. The bound aptamers are eluted and copied by PCR, using the flanking constant region as amplification primer sites. This process is repeated with the enriched aptamer pool until a few aptamers become the majority of the pool. Gel shift assays, fluorescence anisotropy experiments or other binding experiments can be used to determine the affinity of the aptamers for a given target.

The term "% homology" is used interchangeably herein with the term "% identity" herein and normally refers to the level of nucleic acid identity between the nucleic acid sequence of the DNA or RNA aptamers of the present inventions, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence as described herein.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST, and other next generation DNA sequencing analysis programs. Other programs include Galaxy, Lasergene Genomics Suite, CLC Genomics Workbench, DNANexus, GenomeQuest, Softgene NextGENe In certain embodiment, the present invention includes aptamers comprising a nucleotide sequence that is at least 50% identical to a nucleotide sequence selected from the group consisting of: SEQ ID Nos. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, and 66, or any combinations thereof. In certain embodiments, the aptamers comprise a nucleotide sequence that is at least 55%, 60%, 65%, 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9% identical to a nucleotide sequence selected from the group consisting of: SEQ ID Nos. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, and 66, or any combinations thereof.

Exemplary aptamer sequences for lyme detection are provided in Table 1.

TABLE 1

Aptamers directed to OspA, OspC, and BmpA

| | |
|---|---|
| OspA-21 | CATGACACCGTACCTGCTCTAATAAGCACGCCAGGGACTATTAGATCGGAATAGCA CACGTCTGAACTCCAAGCACGCCAGGGACTATTA (SEQ ID NO: 67) |
| OspA-46 | CATGACACCGTACCTGCTCTAATAAGCACGCCAGGGACTATTAGATCGGAAGAGCA CACGTGTGAACTCCAAGCACGCCAGGGACTATTA (SEQ ID NO: 68) |
| OspA-22 | CATGACACCGTACCTGCTCTACGAGATTCAAGCACTCCAGGGACTATTAGATCGGA AGAGCACACGTCTGAAGCACGCCAGGGACTATTA (SEQ ID NO: 69) |
| OspA-39 | CATGACACCGTACCTGCTCTACGAGATTCAAGCACGCCAGGGATTATTAGATCGGA AGAGCACACGTCTGAAGCACGCCAGGGACTATTA (SEQ ID NO: 70) |
| OspA-55 | CATGACACCGTACCTGCTCTTGCTTTTCGTGCGCGCATAAAATACTTTGATACTGTG CCGGATGAAAGCGAAGCACGCCAGGGACTATTA (SEQ ID NO: 71) |
| OspA-59 | CATGACACCGTACCTGCTCTTGCTTTTCGTGCGCGCATAAAATACCTTGATACTGTG CCGTATGAAAGCGAAGCACGCCAGGGACTATTA (SEQ ID NO: 72) |
| OspC-23 | CATGACACCGTACCTGCTCTGCGGTGCTGTATCGTCGTTTAGGCTGTTACCAGGGCC ACCGGACAGAGGTAAGCACGCCAGGGACTATTA (SEQ ID NO: 73) |
| OspC-28 | CATGACACCGTACCTGCTCTCGTATAGATCCTCTCGCGCTTCGGTTTTTAGAAGTAT TCAAGGTATCATCAAGCACGCCAGGGACTATTA (SEQ ID NO: 74) |
| OspC-30 | CATGACACCGTACCTGCTCTGATCAGCCTGGTCAACGGGTGGTCCTGTGCCAAGCT CGAAAATTCGCCGAAAGCACGCCAGGGACTATTA (SEQ ID NO: 75) |
| OspC-34 | CATGACACCGTACCTGCTCTTGGAGCTAGAGAGCCGGTGATCGAAATTCTGGATGT TTCTGACGTTTGCTAAGCACGCCAGGGACTATTA (SEQ ID NO: 76) |
| OspC-36 | CATGACACCGTACCTGCTCTACCCCGGAAATGATTAGCCATTGTGGTACTCATCTGG GCAGTCAGCACATAAGCACGCCAGGGACTATTA (SEQ ID NO: 77) |
| OspC-37 | CATGACACCGTACCTGCTCTTTAACCCCTCGCGGAGGTGTACACGGGCCTACATAA TCCTCCGAGGTTCCAAGCACGCCAGGGACTATTA (SEQ ID NO: 78) |
| BmpA-5 | CATGACACCGTACCTGCTCTTTACGTTTGGGACGTCTGGCGAAGCCACCACAAGCT AGCCCTCCAATTTAAAGCACGCCAGGGACTATTA (SEQ ID NO: 79) |
| BmpA-6 | CATGACACCGTACCTGCTCTTTGATCATCACGGCACACTCATTACGGTTGGATATAC TAGTCCGGTTAGAAAGCACGCCAGGGACTATTA (SEQ ID NO: 80) |
| BmpA-7 | CATGACACCGTACCTGCTCTCCCTTCTGACTGGATGCCGGATCTGGGCCGATTTTGT TCGCGCCCCGCCCAAGCACGCCAGGGACTATTA (SEQ ID NO: 81) |
| BmpA-8 | CATGACACCGTACCTGCTCTTTCCGCTGGTTCCACGTGGTCCCGCGTAGGTTCGTGT GCGCGCAAAATCCAAGCACGCCAGGGACTATTA (SEQ ID NO: 82) |
| BmpA-9 | CATGACACCGTACCTGCTCTGCCCCTGCGTGCCGCAGTCAATCACCATGTTGTTATT ACGGACTACCTGGAAGCACGCCAGGGACTATTA (SEQ ID NO: 83) |
| BmpA-10 | CATGACACCGTACCTGCTCTCCGGTACGATAGGGGTTGAGTTGGACACACTGCCTG GTTAAATTGTGCAGAAGCACGCCAGGGACTATTA (SEQ ID NO: 84) |

In certain embodiment, the present invention includes aptamers comprising a nucleotide sequence that is at least 50% identical to a nucleotide sequence selected from the group consisting of: SEQ ID Nos. 67-84, or any homologue thereof, or any combinations thereof. In certain embodiments, the aptamers comprise a nucleotide sequence that is at least 55%, 60%, 65%, 70%, 75%, 80%, 85%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9%, identical to a nucleotide sequence selected from the group consisting of: SEQ ID Nos. 67-84, or any homologue thereof, or any combinations thereof.

REFERENCES (1) Hofmann, H. P. et al. *RNA* 1997, 3, 1289.
(2) Ellington, A. D. et al. *Nature* 1990, 346, 818.
(3) Geiger, A. et al. *Nucleic Acids Res.* 1996, 24, 1029.
(4) Strehlitz, B. et al. *Bioanal. Rev.* 2012, 4, 1.
(5) Williams, K. P. et al. *Proc. Natl. Acad. Sci.* 1997, 94, 11285.
(6) Purschke, W. G. et al. *Nucleic Acids Res.* 2003, 31, 3027.
(7) Mie, M. et al. *Appl. Biochem. Biotechnol.* 2013, 169, 250.
(8) Ohuchi, S. *Biores Open Access* 2012, 1, 265.
(9) Ikanovic, M. et al. *J. Fluoresc.* 2007, 17, 193.
(10) Kim, Y. S. et al. *Anal. Biochem.* 2013, 436, 22.

D. Raman-Active Marker Molecules

Raman-active markers are chemical moieties covalently attached to one or more aptamers. The markers are typically fluorescent markers that have been incorporated into phosphoramidites (monomers used to build DNA sequences on solid support) designed for incorporation into synthetic oligonucleotides. There are also a second class of Raman active markers, which are not as large (and therefore not as likely to affect the interactions of the aptamer and target) such as alkynes, azides etc. (Yamakoshi (2012) *J Am Chem Soc* 134: 20681-9) that can also be incorporated into synthetic oligo molecules as phosphoramidites. Useful Raman active markers include but are not limited to, Cy3, TAMRA, Texas-Red (TR), Cy3.5, Rhodamine 6G, Cy5. Because so many Raman-active markers are available, many more than with fluorescent dyes, since minor chemical modification of a Raman marker molecule can lead to a new one with a different Raman spectrum even though the two molecules exhibit virtually indistinguishable fluorescence spectra Kneipp et al. *Chem. Rev.* 99, 2957 (1999); Graham et al., *Angew. Chem. Int. Ed.* 39, 1061 (2000). This allows multiplexing by using Raman-active markers with unique spectral signatures for each aptamer or set of aptamers for a given target.

Non-limiting examples of Raman-active markers that can be used for Raman spectroscopy include alkynes, azide, TRIT (tetramethyl rhodamine isothiol), NBD (7-nitrobenz-2-oxa-1,3-diazole), Texas Red (TR) dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, quantum dots, carbon nanotubes and fullerenes. These and other Raman labels may be obtained from commercial sources (e.g., Molecular Probes, Eugene, Oreg.; Sigma Aldrich Chemical Co., St. Louis, Mo.; Glen Research, Sterling, Va.) and/or synthesized by methods known in the art.

Polycyclic aromatic compounds may function as Raman-active markers, as is known in the art. The skilled artisan will realize that the Raman labels used should generate distinguishable Raman spectra and may be specifically bound to or associated with different types of aptamers.

Labels or Raman-active markers may be attached directly to the aptamers or may be attached via various linker compounds during solid phase DNA synthesis. Cross-linking reagents and linker compounds of use in the disclosed methods are known in the art. Raman labels that contain reactive groups designed to covalently react with other molecules, such as the aptamers, are commercially available (e.g., Thermo Scientific, Eugene, Oreg.). Methods for preparing labeled analytes are known (e.g., U.S. Pat. Nos. 4,962,037; 5,405,747; 6,136,543; 6,210,896).

E. Target Definition

As used herein, the term "target" or "analyte" are used interchangeably and mean any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, drugs of abuse, waste product, gunshot residue, and/or contaminant.

In certain embodiments, the analyte or target is present in species of the family *Borrelia*. In certain embodiments, the analyte is a *B. burgdorferi* surface protein selected from OspA, OspB, OspC, BmpA, or combination thereof. OspA, OspB, OspC, and BmpA are outer surface proteins found on *B. burgdorferi*; and they are differentially expressed in humans or within the tick anatomy. OspA and OspB appear to be essentially for survival of *B. burgdorferi* in the tick, and OspC is essential for infection of the mammalian host by infected ticks.

F. Biological Sample

As used herein, the term "biological sample" may include, but is not limited to blood, blood products, serum, plasma, other blood fractions, tissue, tissue extracts, urine, cerebrospinal fluid, saliva, feces, skin, hair, cheek tissue, organ tissue, breath, pleural fluid, sweat, or sputum.

As used herein, a "sample collection apparatus" or "sample collection device" may include, but are not limited to, a swab or other matrix (a filter paper, cotton, pad, or foam), dipstick, test strip, cup, cartridge, capillary, or tube. The biological sample collected or contained therein may be reconstituted, for example in water or a suitable buffer. In certain embodiments, the biological sample does not require reconstitution. The sample collection device may be color coded, e.g. using a dye, detectable tag or bar code, to indicate whether the device is a positive or negative control. In certain embodiments, the matrix or collection device may be made of bonded polyolefin fiber such as Bonded Polyolefin Fibre, Glass Fiber, cellulose, cotton, polyethylene, nylon, natural macromolecules, polyvinyl sulfone, silica, glass fiber, glass fiber with binder, cellulose acetate, or nitrocellulose (NC). The "sample collection apparatus" or "sample collection device" may comprise a housing, wherein said housing may comprise a material suitably adapted for sample collection, such as plastic, and the like.

The sample collection device may further comprise an enzyme or protease, protein, a compound or preservative for processing the biological sample, increasing shelf-life, a chemical stabilizer, diluent, buffer, additive, detergent, lipid, sugar, carbohydrate, or any combination thereof. For example, the enzyme or protease may solubilize the biological or test sample. For example, the enzyme may be, but not limited to, mucin. The protein may be, but not limited to, bovine serum albumin. The preservative may be, but not limited to, sodium azide. Other additives and stabilizers may include, but not limited to, di-sodium hydrogen orthophosphate anhydrous, potassium dihydrogen orthophosphate, d-Mannitol, or any combination thereof.

G. Raman Detectors or Instruments

Analytes may be detected and/or identified by known methods of SERS Raman spectroscopy or other appropriate Raman spectroscopic techniques, such as tip enhanced raman scattering (TERS) and single molecule Raman scattering (SMERS). Variations on surface enhanced Raman spectroscopy (SERS), surface enhanced resonance Raman spectroscopy (SERRS), hyper-Raman spectroscopy and coherent anti-Stokes Raman spectroscopy (CARS) have been disclosed. In SERS and SERRS, the sensitivity of the Raman detection is enhanced by a factor of $10^6$ or more for molecules adsorbed on roughened metal surfaces or nanoparticles, such as silver, gold, platinum, copper or aluminum surfaces. By adding the Raman-active marker to the aptamers in accordance with this invention, there is further and stronger signal enhancement; further the addition of the marker allows identification of the target through the known and distinct spectral characteristics of the marker that is expected to be unique when compared to the matrix surrounding it, or the unmodified aptamer. One useful method of SERS detection is described in U.S. Patent Publication No. 2013/0107254.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the Raman active complex containing one or more analytes. The Raman emission signal is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector, comprising an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source comprises a 514.5 nm line argon-ion laser from SpectraPhysics, Model 166, and a 647.1 nm line of a krypton-ion laser (Innova 70, Coherent).

In certain embodiments, the typical incident wavelengths are about 488, about 514.5, about 532 nm, about 632.8, about 785 nm and about 1064 nm.

Alternative excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam may be spectrally purified with a bandpass filter (Corion) and may be focused on the Raman active complex using a 6× objective lens (Newport, Model L6X). The objective lens may be used to both excite the analytes and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of the complexes of the invention, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

In certain embodiments, the present invention discloses methods for testing whether a point of care testing apparatus, such as a portable Raman detector, is properly functioning. The method comprises the steps of: (a) contacting a sample collection device with water, a buffered solution, or biological sample; (b) inserting the sample collection device into a point of care testing apparatus; and (c) detecting the presence of the positive or negative control, wherein the presence of the positive or negative control indicates that the point of care testing apparatus is properly functioning. In certain embodiments, a standard test cartridge for calibration may be used to test if the point of care testing apparatus is properly functioning.

H. Other Technologies

Current methods to detect the presence of *B. burgdorferi* in ticks use immunological methods to detect bacterial proteins present in tick homogenates. Typically, these tests are time consuming, requiring significant technical skill and training to conduct. Often, ticks are sent into testing laboratories, and it can take weeks for results to be returned; many individuals will have already shown Lyme disease symptoms before they receive the results for the tick testing.

The current accepted method for detecting Lyme disease in humans is based on a CDC-approved, two-tiered serological protocol using whole cell homogenates as targets for the detection of human anti-*B. burgdorferi* antibodies. The first tier tests typically use an ELISA or related assay to detect anti-Lyme IgM or IgG antibodies, and positive or equivocal results will trigger the use of the second test, an IgM or IgG immunoblot using *B. burgdorferi* extracts to detect bands deemed specific for *B. burgdorferi*. A number of problems exist with these serological assays: 1) poor sensitivity; 2) very low levels anti-*B. burgdorferi* antibodies in the first 4-6 weeks of infection; 3) poor anti-*B. burgdorferi* responses in some individuals; 4) subjective interpretation of immunoblots; and 5) the inability to diagnose *B. burgdorferi* infections in antibody treated or re-infected individuals. Because this test detects antibody production and not the pathogen directly, the test cannot detect infections within 3 weeks of infection. Additionally, the test has a specificity >80%, but a sensitivity of only 50-60%. Current estimates in the US suggest that approximately 300,000 human Lyme disease tests are ordered, though many clinicians do not order the test due to the low sensitivity. The low rates at which Lyme disease is reported is in part due to the poor quality of the diagnostic tool currently available to clinicians.

In addition to serologically-based assays, a few other new assays have started to appear in the literature and in the market place. A metabolomics approach to Lyme diagnostics was recently described (Mollins, C. R. et al. *Clin Infect Dis*. 2015 Mar. 11). This method is in early stage development and requires instrument-intensive, technically advanced GC-MS analysis, making point-of-care (POC) detection unlikely. Ceres Nanosciences has developed a nanoparticle-based assay that concentrates Lyme antigens from urine and detects their presence using standard immunoassay technology (Douglas, T. A. et al. *Biomaterials*. 2011 February; 32(4):1157-66; www.ceresnano.com). Although this assay directly detects Lyme antigens instead of anti-*B. burgdorferi* antibodies, the assay uses immunoassay technology to detect Lyme antigens and requiring >4 hrs to conduct, also making POC detection difficult.

A variety of other Lyme disease diagnostic assays have been described in the literature. Some include direct DNA amplification-based assays, culture-based assays, and other direct Lyme antigen detection methods, such as a transistor-based assay that measures Lyme antigen binding to antibody modified carbon nanotubes (Lerner, M. B. et al. *Biosens Bioelectron.* 2013 Jul. 15; 45:163-7). Many of these assays are in early stages of development or have yielded results inferior to the current CDC-approved two-tiered immunoassay.

The present invention has several advantages of the methods described above, including: 1) DNA aptamers provide a high affinity, flexible, and easily generated and modified alternative to anti-Lyme antigen antibodies used in other detection systems; 2) the nanoparticle-based antigen binding allows for easy and rapid binding and separation of the antigens from bulk blood, serum or plasma; 3) the $10^6$ to $10^{14}$-fold signal amplification of SERS allows for ultra-sensitive Lyme antigen detection; 4) the proprietary placement Raman labels along the DNA aptamers dramatically improves specificity and sensitivity of the SERS-based detection; and 5) the entire detection method, from antigen binding to SERS detection takes <30 minutes, making it highly appropriate for POC diagnostic applications.

As can be appreciated from the disclosure above, the present invention has a wide variety of applications. The invention is further illustrated by the following examples, which are only illustrative and are not intended to limit the definition and scope of the invention in any way.

EXEMPLIFICATIONS

I. Reagents and Methods for Detecting Infectious Diseases (Examples 1-4)

Example 1

Aptamer Selection for Oxytocin (OT) and Oxytocin-Gly-Lys-Arg (OT-GKR)

Aptamers against OT and OT-GKR were selected by adapting the selection process described by Hoon et al.[1] In this method, biotin-OT and biotin-OT-GKR are bound to magnetic, biotinylated microspheres, and these microspheres act as an easily collected substrate to separate DNA oligonucleotides bound to the peptide hormones from unbound oligos. The oligonucleotide pool used as the aptamer selection library consisted of 40 random nucleotides flanked by short stretches of constant DNA sequences which can act as primer sites necessary for PCR amplification of the aptamer library following aptamer selection. The sequence of the aptamer library was: 5'-ACACTCTTTCCC-TACACGACGCTCTTCCGATCT-[N]$_{40}$-AGATCG-GAAGAGCACACG TCTGAACTCCAGTCAC-3' (SEQ ID NO: 1) Flanking regions for this oligo were chosen to be complementary to the adapter sequences for next generation sequencing (NGS) of DNA on the Illumina MiSeq sequencing platform. Briefly, the aptamer selection process is as follows:

- 0.1 ml of Dynabeads m270 are used for each round of selection against a target, and 0.1 ml Dynabeads are used for each negative selection
- Dynabeads are washed 3 times with PBS
- Dynabeads for positive selection are incubated (with constant rotation) with 100 pmol biotin-OT or biotin-OT-GKR in PBS for 30 min at room temperature
- Peptide bound Dynabeads are washed 3 times with PBS
- All Dynabeads samples (OT, OT-OKR, and 2 samples for negative control) are washed 2 times with PBS+0.1% BSA
- Aptamer Selection Library DNA (in the first round of selection 15 nmol of DNA is used for each selection; in subsequent selection rounds 90% of the aptamer library collected from the previous round is used) is incubated at 95° C. for 5 min, 0° C. for 5 min, and room temperature for 5 min
- DNA is added to the negative control Dynabeads and incubated at room temperature for 30 min with constant rotation
- The supernatant from the negative selection Dynabeads is transferred to either the OT or OT-GKR bound Dynabeads—samples are incubated at room temperature for 30 min with constant rotation
- Supernatant is removed from the Dynabeads and the Dynabeads are washed 3 times with PBS+0.1% BSA and 1 time with PBS
- Dynabeads with bound aptamer library DNA is stored at −20° C. until ready for PCR amplification and analysis
- Following PCR analysis, approximately 20% of each sample is sent for NGS DNA sequencing on an Illumina MiSeq instrument and the remaining fraction was used to generate single stranded DNA (ssDNA) to be used in the next round of aptamer selection
- ssDNA is generated using asymmetric PCR followed by Lambda Exonuclease digestion of the reverse complement strand of DNA High Throughput DNA Sequencing Following aptamer selection, oligonucleotides bound to the Dynabeads are PCR-amplified using primers that add the Illumina TruSeq Universal Adapter sequence to the 5'-end of the oligo and a TruSeq Indexed primer containing a 6-base barcode to the 3'-end of the oligo. Table 1.3 shows four samples that are generated for NGS analysis. Underlined sequences represent the 6 base barcodes that are required to distinguish pooled samples on the DNA sequencing procedure.

TABLE 1.3

Reverse PCR Primer Oligonucleotides Showing TruSeq Index Barcodes

| Sample | Index No. | Primer Sequence |
|---|---|---|
| Oxytocin | 6 | CAAGCAGAAGACGGCATACGAGAT<u>ATTGGC</u>GTGACTGGAGTTCAGACGT GTGCTCTTCCGATCT (SEQ ID NO: 2) |
| Oxytocin-GKR | 7 | CAAGCAGAAGACGGCATACGAGAT<u>GATCTG</u>GTGACTGGAGTTCAGACGT GTGCTCTTCCGATCT (SEQ ID NO: 3) |

TABLE 1.3-continued

Reverse PCR Primer Oligonucleotides Showing TruSeq Index Barcodes

| Sample | Index No. | Primer Sequence |
|---|---|---|
| Negative Control | 12 | CAAGCAGAAGACGGCATACGAGATTACAAGGTGACTGGAGTTCAGACGT GTGCTCTTCCGATCT (SEQ ID NO: 4) |
| Aptamer Library | 17 | CAAGCAGAAGACGGCATACGAGATCTCTACGTGACTGGAGTTCAGACGT GTGCTCTTCCGATCT (SEQ ID NO: 5) |

Following PCR amplification, the samples are sequenced. Approximately equimolar amounts of the four samples are pooled and run on a single lane of the MiSeq sequencer, which is capable of sequencing 20,000,000 DNA strands in an overnight analysis. The instrument is set to read sequences up to 50 bp in length, allowing the random sequence to be determined in its entirety with every sequencing reaction. Sequences associated with each sample are identified by the 6 base barcode added to the aptamer by PCR prior to the sequencing reaction. Bioinformatics To analyze the sequence data generated by the Illumina MiSeq high-throughput DNA sequencer, analytical tools for aptamer analysis were developed by adapting the methods described in Latulippe et al.[4]

First, the data from the Illumina MiSeq DNA sequencer are sorted by DNA barcode and mathematically filtered to remove artifactual sequences, such as sequences that contained long stretches of homopolymers. Then all sequences from a single sample are compared and all exact matches within a sample are counted and sorted by the number of times the sequence occurs. The most common 5000 sequences from each sample are exported into Microsoft Excel. The number of occurrences of a specific sequence is normalized for each sample against the total number of sequences that are generated for each sample (i.e. OT, OT-GKR, or negative control). The most commonly occurring samples from the OT selection are compared with sequences from the OT-GKR selection and the Negative control selection, and sequences that are unique to the OT selection are highlighted. These sequences are labeled as potential OT aptamers. The same analysis is used to analyze the OT-GKR selection to generate aptamers that are potential OT-GKR aptamers.

Table 1.4 shows the results from these analyses. Of the top 30 sequences, only one oxytocin aptamer sequence is both unique to the OT library and absent from the top 5000 negative control sequences (oligo number followed by R). Two additional sequences were unique to OT and were only rarely (fewer than 5 times out of ~5×10$^6$ sequences) found in the negative control sequences (oligo number followed by Y). For the top 30 OT-GKR sequences, two unique sequences were found and one sequence was found that was unique to OT and was only rarely found in the negative control sequences.

Based on the results shown in Table 1.4, the following oligonucleotides are synthesized and tested for OT and OT-GKR binding:

Oxytocin (SEQ ID NO: 6)
5'-ATGCAAATTAGCATAAGCAGCTTGCAGACCCATAATGTC-3'

(SEQ ID NO: 7)
5'-ATAGTGTTATTAATATCAAGTTGGGGGAGCACATTGTAG-3'

(SEQ ID NO: 8)
5'-CTTGTTTACGAATTAAATCGAAGTGGACTGCTGGCGGAA-3'

Oxytocin-GKR (SEQ ID NO: 9)
5'-TAAACGTGACGATGAGGGACATAAAAAGTAAAAATGTCT-3'

(SEQ ID NO: 6)
5'-ATGCAAATTAGCATAAGCAGCTTGCAGACCCATAATGTC-3'

(SEQ ID NO: 11)
5'-AGTTGCCATACAAAACAGGGTCGCCAGCAATATCGGTAT-3'

TABLE 1.4

Results of Sequence Comparisons of Aptamers Obtained from Illumina MiSeq DNA Sequencing

| Oxytocin | | Oxytocin-GKR | |
|---|---|---|---|
| No of Oligos | Oligo Sequences | No of Oligos | Oligo Sequences |
| 18 | TAGCCACATAGAAACCAACAGCCATATAACTGGT AGCTT(SEQ ID NO: 12) | 18 | TTTCCTGCTCCTGTTGAGTTTATTGCTGCCGTCATT GCT(SEQ ID NO: 39) |
| 17 | CATAATGTCAATAGATGTGGTAGAAGTCGTCATTT GGCG(SEQ ID NO: 13) | 17 | GGTCAGTAGCAATCCAAACTTTGTTACTCGTCAGA AAAT(SEQ ID NO: 40) |
| 17 | TAATAACCTGATTCAGCGAAACCAATCCGCGGCAT TTAG(SEQ ID NO: 14) | 17 | AAATAGTTGTTATAGATATTCAAATAACCCTGAAA CAAA(SEQ ID NO: 41) |
| 16 | CACAGTCCTTGACGGTATAATAACCACCATCATGG CGAC(SEQ ID NO: 15) | 16 | GGGAGGGTAGTCGGAACCGAAGAAGACTCAAAG CGAACC(SEQ ID NO: 42) |
| 16 | GCGGCGGCAAGTTGCCATACAAAACAGGGTCGCC AGCAA(SEQ ID NO: 16) | 15 | GTCATTTGGCGAGAAAGCTCAGTCTCAGGAGGAA GCGGA(SEQ ID NO: 43) |

TABLE 1.4-continued

Results of Sequence Comparisons of Aptamers Obtained from Illumina MiSeq DNA Sequencing

| \multicolumn{2}{c}{Oxytocin} | \multicolumn{2}{c}{Oxytocin-GKR} |
|---|---|---|---|
| No of Oligos | Oligo Sequences | No of Oligos | Oligo Sequences |
| 16 | TATTTAACTGGCGGCGATTGCGTACCCGACGACCAAAAT (SEQ ID NO: 17) | 15 | CGGCGTACGGGGAAGGACGTCAATAGTCACACAGTCCTT (SEQ ID NO: 44) |
| 15 | AAGAGCAGAAGCAATACCGCCAGCAATAGCACCAAACAT (SEQ ID NO: 18) | 14 | ATAATCTCTTTAATAACCTGATTCAGCGAAACCAATCCG (SEQ ID NO: 45) |
| 15 | CAGCGAAACCAATCCGCGGCATTTAGTAGCGGTAAAGTT (SEQ ID NO: 19) | 14* | TAAACGTGACGATGAGGGACATAAAAAGTAAAAATGTCT (SEQ ID NO: 9) |
| 14 | TATGGCTAAAGCTGGTAAAGGACTTCTTGAAGGTACGTT (SEQ ID NO: 20) | 14 | ATTAGCTGTACCATACTCAGGCACACAAAAATACTGATA (SEQ ID NO: 46) |
| 14** | ATAGTGTTATTAATATCAAGTTGGGGGAGCACATTGTAG (SEQ ID NO: 7) | 14 | TTGTTATAGATATTCAAATAACCCTGAAACAAATGCTTA (SEQ ID NO: 47) |
| 14 | ATGGAAATGAAGACGGCCATTAGCTGTACCATACTCAGG (SEQ ID NO: 21) | 13 | TGTAGCGAACTGCGATGGGCATACTGTAACCATAAGGCC (SEQ ID NO: 48) |
| 13 | CTCTTTAGTCGCAGTAGGCGGAAAACGAACAAGCGCAAG (SEQ ID NO: 22) | 13 | AGCTTACTAAAATGCAACTGGACAATCAGAAAGAGATTG (SEQ ID NO: 49) |
| 13 | ACGAAAGACCAGGTATATGCACAAAATGAGATGCTTGCT (SEQ ID NO: 23) | 13 | TCAATAGCAGGTTTAAGAGCCTCGATACGCTCAAAGTCA (SEQ ID NO: 50) |
| 13 | CATATAACTGGTAGCTTTAAGCGGCTCACCTTTAGCATC (SEQ ID NO: 24) | 13 | CCGCTTCGGCGTTATAACCTCACACTCAATCTTTTATCA (SEQ ID NO: 51) |
| 13 | TGAAACCAACATAAACATTATTGCCCGGCGTACGGGGAA (SEQ ID NO: 25) | 13 | TATCAGGGTTAATCGTGCCAAGAAAAGCGGCATGGTCAA (SEQ ID NO: 52) |
| 12 | TTTAGCCATAGCACCAGAAACAAAACTAGGGACGGCCTC (SEQ ID NO: 26) | 12** | AGTTGCCATACAAAACAGGGTCGCCAGCAATATCGGTAT (SEQ ID NO: 11) |
| 12 | TTTAGTCGCAGTAGGCGGAAAACGAACAAGCGCAAGAGT (SEQ ID NO: 27) | 12 | CACCAAACATAAATCACCTCACTTAAGTGGCTGGAGACA (SEQ ID NO: 53) |
| 12 | AAGCACCTTTAGCGTTAAGGTACTGAATCTCTTTAGTCG (SEQ ID NO: 28) | 12 | TCCATATCTGACTTTTTGTTAACGTATTTAGCCACATAG (SEQ ID NO: 54) |
| 12 | ATTCTTTAGCTCCTAGACCTTTAGCAGCAAGGTCCATAT (SEQ ID NO: 29) | 12 | AATAATGTTTATGTTGGTTTCATGGTTTGGTCTAACTTT (SEQ ID NO: 55) |
| 12 | ATTGGTATCAGGGTTAATCGTGCCAAGAAAAGCGGCATG (SEQ ID NO: 30) | 12 | ACGTTAACAAAAGTCAGATATGGACCTTGCTGCTAAAG (SEQ ID NO: 56) |
| 12 | CAGATATTGAAGCAGAACGCAAAAGAGAGATGAGATTG (SEQ ID NO: 31) | 12 | ACGTTGGCTGACGACCGATTAGAGGCGTTTTATGATAAT (SEQ ID NO: 57) |
| 11 | AAAAACGATAAACCAACCATCAGCATGAGCCTGTCGCAT (SEQ ID NO: 32) | 12 | CATGGTGGCGAATAAGTACGCGTTCTTGCAAATCACCAG (SEQ ID NO: 58) |
| 11* | ATGCAAATTAGCATAAGCAGCTTGCAGACCCATAATGTC (SEQ ID NO: 6) | 12 | CGGGCAATAATGTTTATGTTGGTTTCATGGTTTGGTCTA (SEQ ID NO: 59) |
| 11 | CAGTAGGCGGAAAACGAACAAGCGCAAGAGTAAACATAG (SEQ ID NO: 33) | 12 | GCGATGGGCATACTGTAACCATAAGGCCACGTATTTTGC (SEQ ID NO: 60) |
| 11 | CCTCACTTAAGTGGCTGGAGACAAATAATCTCTTTAATA (SEQ ID NO: 34) | 11 | AACAAAAGTCAGATATGGACCTTGCTGCTAAAGGTCTA (SEQ ID NO: 61) |
| 11** | CTTGTTTACGAATTAAATCGAAGTGGACTGCTGGCGGAA (SEQ ID NO: 8) | 11 | ACGCGGCACAGAATGTTTATAGGTCTGTTGAACACGACC (SEQ ID NO: 62) |
| 11 | GAAGTGCCAGCCTGCAACGTACCTTCAAGAAGTCCTTTA (SEQ ID NO: 35) | 11 | ATGGTGGCGAATAAGTACGCGTTCTTGCAAATCACCAGA (SEQ ID NO: 63) |
| 11 | GCATCATCTTGATTAAGCTCATTAGGGTTAGCCTCGGTA (SEQ ID NO: 36) | 11 | CCGCCAGTTAAATAGCTTGCAAAATACGTGGCCTTATGG (SEQ ID NO: 64) |
| 11 | GGATTTGAGAATCAAAAGAGCTTACTAAAATGCAACTG (SEQ ID NO: 37) | 11 | TAACAGATACAAACTCATCACGAACGTCAGAAGCAGCCT (SEQ ID NO: 66) |

TABLE 1.4-continued

Results of Sequence Comparisons of Aptamers Obtained from Illumina MiSeq DNA Sequencing

| Oxytocin | | Oxytocin-GKR | |
|---|---|---|---|
| No of Oligos | Oligo Sequences | No of Oligos | Oligo Sequences |
| 11 | TGACCAGCAAGGAAGCCAAGATGGGAAAGGTCATGCGGC(SEQ ID NO: 38) | 11* | TTTTAAAGCGCCGTGGATGCCTGACCGTACCGAGGCTAA(SEQ ID NO: 10) |

Notes: =
*= Unique sequences, not found in the other OT peptide or Negative control sequences
**= Unique sequences in other OT peptide and found in low levels in the Negative Control sequences Example 2

Synthesis of, and Oxytocin Detection with, Aptamer-Modified Silver Nanoparticles (Ag-NPs)

Synthesis of the Ag NPs were performed using the literature procedure described by Leona,[5] in which the NPs were synthesize through reduction of silver sulfate in the presence of glucose and citrate. Briefly, the synthetic method involved the precipitation of silver sulfate from an aqueous solution of silver nitrate through the addition of sulfuric acid. A $5\times10^{-4}$ M aqueous solution of the freshly precipitated silver sulfate salt was prepared, and 12.5 mL of this solution was mixed with 1% solutions of citrate (1 mL) and glucose (500 µL). The solution was heated using a microwave digestion system (Anton Parr Multiwave 3000), using three heating programs in which the temperature of the solution was ramped to 120° C. over 30 seconds, and held at this temperature for 30, 60 or 90 seconds. The NPs were then purified by centrifugation for 15 minutes, after which the supernatant was removed and replaced with distilled deionized water to reduce the citrate concentration.

Each of the temperature programs resulted in Ag NPs that demonstrated spectroscopic characteristics that compared favorably with those reported in the literature (FIG. 5, Panel A and Panel B).[5,6] The absorption maximum was found at 401 nm, with a full maximum at half with value of 60 nm, which compares favorably with the 56 nm value from the literature.[5] Since the plasmon resonance is intimately related to the particle size, the NPs are determined to be 20 to 25 nm based on these data by comparison with literature.[7]

Figure 5A:
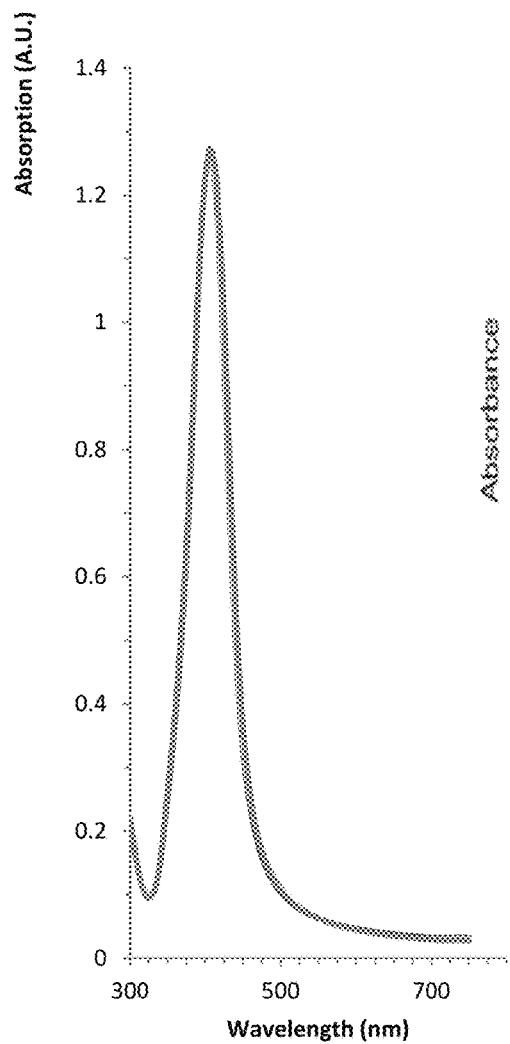
FIG. 5 contains two panels. Panel A depicts absorption spectrum of silver NPs produced using the microwave-based synthetic methods in which the solution was heated to 120° C. over 30 seconds, and held at this temperature for 30, 60 and 90 seconds. The NPs produced exhibit spectral characteristics (401 nm; FWHM=60 nm) that compare favorably with spectra from literature. Panel B depicts an example absorption spectrum of microwave synthesized Ag NPs from Leona, M. *Proc. Natl. Acad. Sci.* 2009, 106, 14757.
Figure 5B:
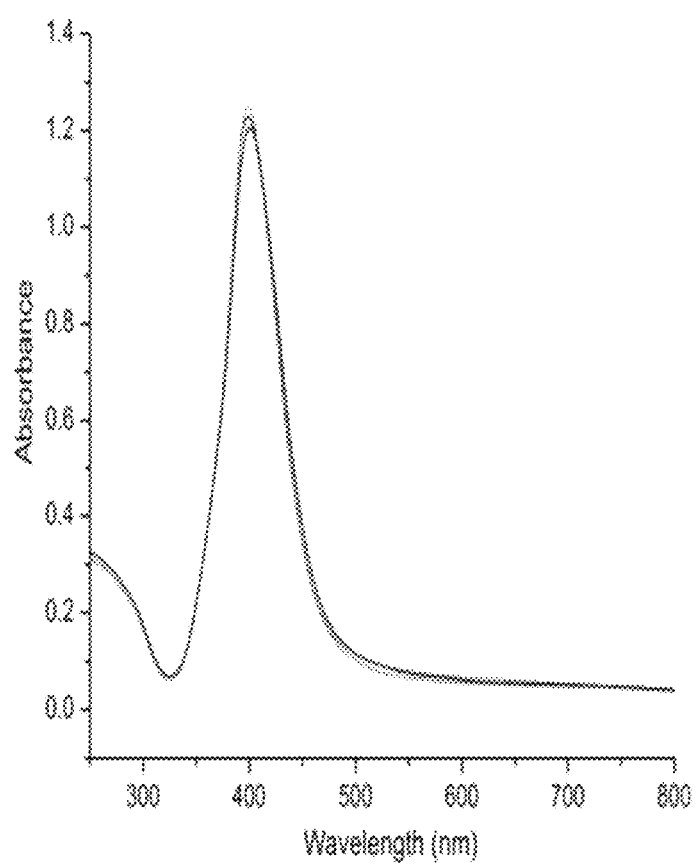
Figure 6A:
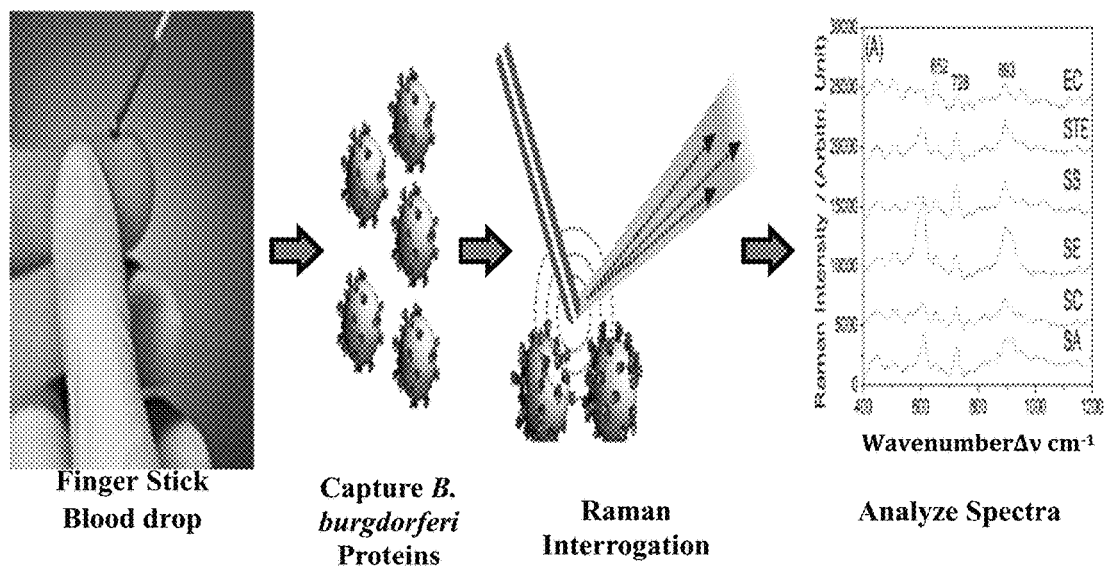
FIG. 6 contains two panels. Panel A depicts a schematic representation of the SERS-based detection of *Borrelia burgdorferi* from human blood. Drops of blood, serum, or plasma are used directly for the detection of *B. burgdorferi*-specific proteins. Blood, serum, or plasma is exposed to aptamer coated SERS-active surface, filtered, and interrogated by Raman spectroscopy. Spectra are analyzed on a small instrument and results are available in <30 min. Panel B depicts a schematic representation of the proposed SERS-based detection of *Borrelia burgdorferi* in *Ixodes scapularis* nymphs. Blacklegged tick nymphs are collected and lysed. The homogenate is mixed with aptamer coated nanoparticles, and interrogated by Raman spectroscopy. Spectra are analyzed on the portable instrument and results are available in <20 min.
Figure 6B:
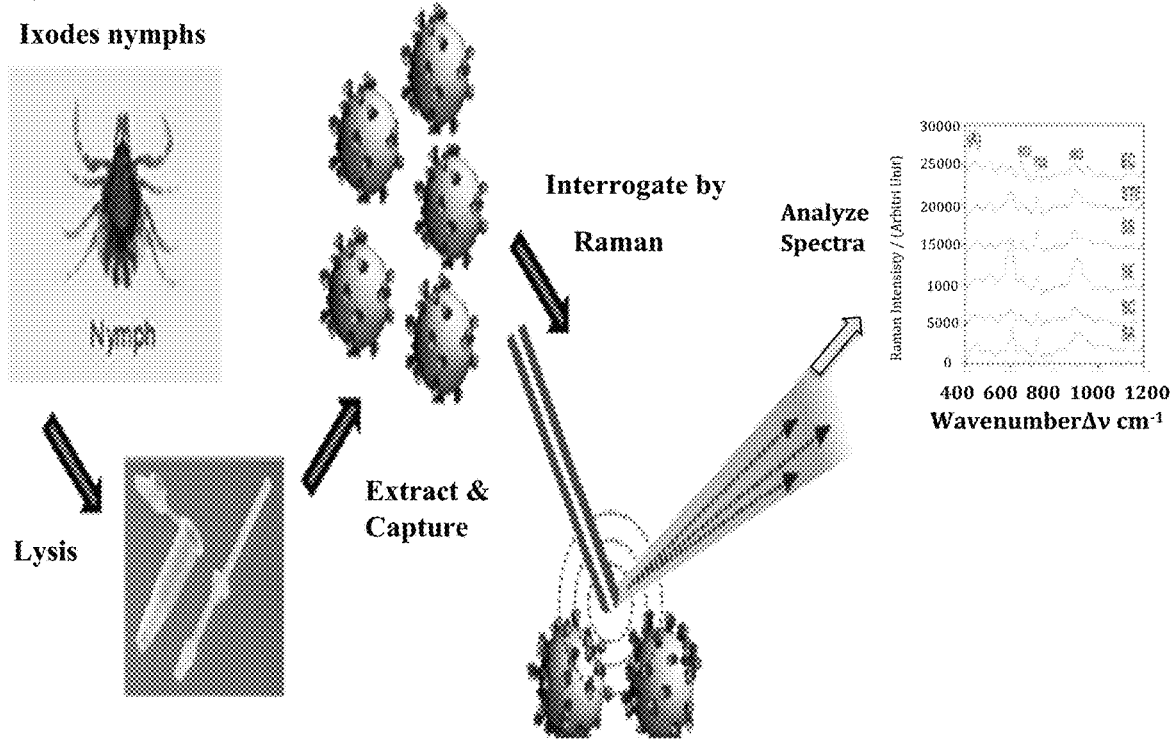

The absorption spectra of the NPs were collected three weeks after the synthesis was initially performed to demonstrate the stability of the NPs. Absorption spectra of NPs stored in the reaction mixture before centrifugation, with high citrate and glucose concentrations, and those that had been centrifuged on the day the NPs had been synthesized, to lower citrate concentrations, were compared (FIG. 5, Panel A). The similarity of the absorption spectra with each other, and with the spectrum collected the day of the synthesis, indicates the microwave-based synthetic method produce stable Ag NPs capable of serving as the basis of a robust method for oxytocin detection.

The ability of these Ag NPs to produce Raman enhancement was then demonstrated using a model SERS active compound, mercaptophenol (MCP). MCP was used in these studies for two important reasons: it produces a signature Raman spectrum that allows the efficacy of the NPs as SERS substrates to be determined, and it interacts with the Ag NPs through a thiol linkage analogous to the one used to modify the surface of Ag NPs with thiolated aptamers. The spectrum of a 200 µM solution of MCP collected in the presence of the Ag NPs and a 100 µM solution of potassium nitrate was compared to the spectrum of the same solution in the absence of the NPs, demonstrating a five order of magnitude enhancement provided by the presence of the NPs (FIG. 2, Panel B).

Building on the successful synthesis of the Ag NPs were performed using the literature procedure described by Leona,[5] and demonstration of the ability of the synthesized Ag NPs to produce a five order of magnitude increase in spectral intensity, this facet of the research focused on the modification of Ag and Au NPs with thiolated DNA. Thiolated DNA is typically synthesized using a disulfide moiety, requiring the reduction of the disufide to the thiol or dithiol moiety in anticipation of modifying NP surfaces with the oligonucleotide. In order to perform the reduction, three methods were applied: the first involved the reduction of the disulfide with: dithiothreitol (DTT) under basic conditions,[8] tris(2-carboxyethyl)phosphine (TCEP) under acidic conditions,[9] or simply exposing the disulfide terminated DNA to the NPs to facilitate reduction of the disulfide.[10]

Investigation of the efficacy of the surface modification were performed using DNA modified with oligonucleotides that are terminated with either mono- or dithiol-moieities. The efficacy of this approach was monitored using absorption spectroscopy. Surface modification of the NPs generally involves incubation of the NPs in the presence of thiol-modified DNA for 16-24 hrs., followed by slow addition of salt to facilitate an increase of DNA concentration at the NP surface. The slow addition of salt, typically in 50 mM increments over the span of 2-5 days to a final concentration of 300 mM, is intended to increase the concentration of DNA at the NP surface by balancing the charge of the phosphate moieites in the DNA backbone, reducing repulsion. Salt conditions may be adjusted to produce DNA-modified NP SERS substrates.

Comparison of the monothiol- and dithiol-terminated oligonucleotides, involved investigation of two parameters in the surface modification with the dithiol-terminated oligonucleotides: the reducing agent used to activate the disulfide modifier, and the rate and concentration of the salt to increase the concentration of DNA at the NP surface. The efficacy of the surface modification was monitored by measuring the retention of the surface plasmon absorption. The initial step, in which the disulfide modified DNA was reduced to produce the dithiol terminus capable of ligating the Ag NP surface, was performed in the presence of dithiothretol (DTT),[9] (tris(2-carboxyethyl)phosphine) (TCEP),[8] and in the absence of reducing agent by direct exposure of the disulfide to the NP suspension.[10]

As illustrated in FIG. 2, Panel C, the plasmon is stable after exposure to both dithiol-terminated DNA and the addition of 25 mM NaCl. Increasing the concentration to 50 mM salt results in the first shift of the plasmon absorption to lower energy. Further addition of salt, bringing the salt concentration to a total of 100 mM, results in rapid loss of the plasmon indicative of NP aggregation.

Each of the approaches were performed in parallel and monitored using absorption spectroscopy (FIG. 2, Panel D). While the intensity of the surface plasmon indicated that each of the reduction methods resulted in successful addition of the dithiol-modified DNA, there were significant differences noted when sodium chloride was added to increase the concentration of DNA at the NP surface. Addition of sodium chloride in 25 mM aliquots to Ag NPs modified in the absence of reducing agent, or in the presence of TCEP did not significantly decrease the intensity of the plasmon absorption, however NPs that had been exposed to the dithiol-modified DNA reduced with DTT resulted in a significant decrease in the plasmon absorption. A comparison of the changes in plasmon absorption intensity upon addition of sodium chloride to NPs modified in the presence of various disulfide reducing conditions (FIG. 2, Panel E), confirms that NPs prepared either with TCEP or in the absence of reducing agents results in the best retention of the Ag NP plasmon.

The surface modification of the NPs was confirmed in two ways: first, a control experiment in which NPs that had not been exposed to dithiol-terminated DNA was exposed to the same sodium chloride addition conditions as the DNA modified NPs. This resulted in significant loss of plasmon intensity upon addition of 25 mM sodium chloride (FIG. 2, Panel E). The second demonstration of the surface modification exploited the presence of the fluorescent FAM marker present at the 5'-terminus. Following the protocol established by Mirkin and co-workers, the FAM-modified DNA was removed from the surfaces of the Ag NPs by exposing the DNA-modified NPs to a 0.1 M solution of DTT.[11] Following centrifugation of the sample to separate the Ag from the supernatant, the flourescence of the solution was measured upon irradiation with 488 nm light (FIG. 2, Panel F). The resulting emission spectrum demonstrates the successful modification of the NP surface with the dithiol-modified DNA. The relative intensities of the emission spectra suggest the surface modification is most effective in the absence of reducing agent, confirming what was observed in the absorption study.

The methods developed herein facilitate the reliable modification of Raman active Ag NPs with mono-thiol or dithiol-terminated aptamer oligonucleotides. Dithiol-terminated oligos produce NPs that are more stable than the mono-thiol terminated oligos, and may be employed in all subsequent optimization of surface modification procedures. The dithiol-modified DNA aptamer proxy was also modified with a fluorescent marker, FAM, at the 5'-terminus. The disulfide modifier has been shown to be more effective at anchoring DNA at the NP surface,[10] and FAM-terminated DNA has been used to demonstrate the presence of DNA at NP surfaces through fluorescence experiments.[11] Based on these results, Ag NPs prepared in the absence of reducing agent and with 50 mM NaCl added to increase the concentration of DNA at the NP surface were used in all subsequent Raman studies.

Example 3

Sample Preparation for User Ease and Increased Sensitivity

Bringing NPs into close proximity to form "hot spots" through the addition of common inorganic salts is well suited to this application. The addition of salt has been suggested to result in the aggregation of NPs in solution, with the resulting proximity of the NPs resulting in the "sharing" of NP plasmons, increasing enhancement of the vibrational spectrum beyond that observed in the presence of individual, SERS-active NPs.

To illustrate the effect of salt on the efficacy of the NPs to produce the Raman scattering enhancement, the effect of adding 100 µM solutions of two common salts, potassium nitrate and sodium chloride, was investigated. As shown in FIG. 3, Panel A, the addition of both salts resulted in an increase of an order of magnitude of the spectral intensity, with the potassium nitrate producing spectral intensity 60% higher than that produced upon introduction of sodium chloride. These results formed the basis of the methods established in this effort.

Based on the success of the DNA modification method development, Raman interrogations of the resulting materials were interrogated using 632.8 nm and 785 nm incident wavelengths, revealing the presence of distinct, reproducible spectral features suggestive of a discrete molecule such as the fluorescent FAM incorporated into our sequence at the 5' terminus. The ability to observe features indicative of a dye marker in the presence of oligonucleotides has been demonstrated by Mirkin and co-workers for multiple dyes, and has used this for multiplexing based on the intense, distinctive features associated with the dyes.[12]

The first study was performed to determine which salt additive introduced just prior to spectral analysis provided the largest spectral features. As illustrated in FIG. 3, Panel B, the addition of $KNO_3$ produces a higher intensity Raman feature, likely due to "hot spot" formation, leading to a synergistic increase in spectral intensity. In keeping with this observation, spectral features observed with the Ag NPs modified with 5'-FAM terminated DNA were most intense in the presence of $KNO_3$.

The strong spectral features demonstrated by FAM provide the opportunity for development of a method for detection of oxytocin. The sharp, intense spectral features of 5'-FAM rivals the intensity of mercaptophenol (MCP), and provides spectral features which can be used as a proxy for the analytical target. The interaction of the FAM-modified aptamer with the aptamer target induces changes in the intensity of the FAM-derived spectral features.

To produce a Ag NP surface monolayer in which both the FAM- and MCP-derived spectral features were observed, the FAM DNA-modified Ag NPs were exposed to varying concentrations of MCP. Mixed monolayers at Ag NP surfaces composed of FAM-modified and MCP concentrations ranging from 4 mM to 4 µM were investigated, with the presence of both MCP and FAM spectral features observed most effectively with a concentration of 4 µM MCP (FIG. 3, Panel C). The mixed MCP/FAM DNA monolayer at the NP surface revealed demonstrated distinct, easily differentiable spectral features from MCP and FAM (FIG. 3, Panel D). Features at 714 $cm^{-1}$ and 1050 $cm^{-1}$ are derived from the FAM dye found at the 5'-terminus of the dithiol-modified DNA, whereas the features at 613 $cm^{-1}$, 1010 $cm^{-1}$, 1080 $cm^{-1}$ and 1175 $cm^{-1}$ are contributions from the MCP monolayer. The presence of these two distinct groups of features suggests these can be used for ratiometric quantitation, where FAM modified DNA-derived features will change upon introduction of the analyte, while the MCP features will remain constant.

Further investigation of the system with using 785 nm incident light revealed a similar set of spectral features. The ability to translate these spectroscopic features to the lower energy incident light is important as the instrumentation using this incident wavelength is commerically available, relatively inexpensive and readily accessible for use by those that have little training in spectroscopy. The spectrum collected of Ag NPs with surface monolayers composed of 4 mM MCP and the FAM-modified DNA again demonstrated spectral features that could readily be assigned to the two components of the mixed monolayer. The FAM-modified DNA contributed features at 305 $cm^{-1}$, 714 $cm^{-1}$ and 1050 $cm^{-1}$, whereas the MCP contributed features at 393 $cm^{-1}$, 636 $cm^{-1}$, 1010 $cm^{-1}$, 1080 $cm^{-1}$ and 1175 $cm^{-1}$. These spectra reveal features that are similar to those observed under 633 nm irradiation, as well as additional features specific to the 785 nm spectra (FIG. 3, Panel E).

A second aspect of the spectral optimization process, the effect of mixed monolayers composed of Raman-labeled DNA coupled with either MCH or MCP, signal intensity of the monolayer, as well as the effect of further modification of the surface monolayer was investigated. The work of Lin and co-workers, in which the addition of mercaptohexanol was demonstrated to improve the Raman intensity of dye-modified vasopresin using Raman spectroscopy,[13] served as the basis for investigation of a variety of surface modifications and new substrates, revealing further improvements in the spectroscopic methods for this application.

The first approach investigated as a method to increase Raman signal intensity involved adding 1-mercaptohexan-6-ol (MCH) to FAM-DNA-modified Ag NPs. The addition of this molecule to the surface monolayer has resulted in increased signal intensity in previous Raman-based detection schemes which rely on apatamers for target recognition.[13]

Three concentrations of MCH: 400 µM, 40 µM and 4 µM, were added to the DNA-modified Ag NPs, revealing a significant increase in the intensity of two FAM-derived spectral features, at 714 $cm^{-1}$ and 1050 $cm^{-1}$, at all three concentrations. The largest increase was observed at the lowest concentration (FIG. 3, Panel F) and is consistent with previous observations of thiolated molecules displacing DNA at the NP surface. This phenomenon was exploited to displace FAM-modified DNA from the Ag NP surface to demonstrate successful surface modification of the NP (FIG. 2, Panel F).

An investigation parallel to the one studying the effect of MCH on the Raman intensity of Ag NPs with mixed surface monolayers composed of FAM-DNA, a proxy for the dye-modified aptamer, was performed using MCP, the internal standard against which oxytocin can be quantified, was executed. To identify the optimal surface layer composition, the baseline corrected intensities of the two largest spectral features associated with the MCP and FAM, 1050 $cm^{-1}$ and 1080 $cm^{-1}$ respectively, were compared with varying concentrations of MCH and MCP added to the FAM-DNA modified Ag NPs.

Three concentrations of MCP ranging from 4 to 400 µM, and two concentrations of MCH, 4 and 40 µM were tested. This comparison revealed the largest enhancements of both the MCP and FAM DNA spectral features were observed with addition of intermediate concentration of MCP, 40 µM (FIG. 3, Panel F). While it is intuitive that the addition of the lowest concentration of MCP (4 µM) results in a less intense 1080 $cm^{-1}$ feature, since there is less MCP available for surface modification, there is also a decrease in the spectral intensity with an increase in the concentration of MCP to 400 µM, suggesting competition between thiolated molecules at the NP surface. The effect of the competition is also reflected in FAM-derived Raman intensities: addition of 400 µM MCP results in lower intensity, while addition of 4 µM MCP results in minimal changes in the intensity of the 1050 $cm^{-1}$ feature.

In summary, these investigations provide an understanding of the parameters necessary to optimize SERS-based quantitative determination of oxytocin levels with aptamer-modified Ag NPs were undertaken. The first involved investigating the effect of adding thiolated molecules to the surface of FAM-DNA-modified Ag NPs. Two molecular components were tested: MCP, an internal standard molecule and MCH, a molecule capable of filling unoccupied spaces on the NP surface and facilitating organization of the molecules at the surface. This study revealed a need for a balance between the concentrations of the two molecular components to provide optimal signal intensity for the FAM and MCP features.

Example 4

Efficacy of Aptamer-Modified NP-Based Oxytocin Detection

Using the conditions established in Example 3, a process for identification and quantitation from a buffer solution containing the targets, as well as bovine serum albumin are investigated. Concentrations of vasopressin, as a proxy for oxytocin, is investigated over a concentration range spanning nM to µM solutions, to both prepare a standard curve, and to determine the limit of detection of the proposed approach. The method is developed using the 9-amino acid oxytocin peptide, and extended for use with the 12-amino acid pro-oxytocin.

In preparation for testing the oxytocin-targeting aptamer, initial investigations of Raman-based hormone detection are performed using vasopressin-targeting aptamers reported in He et al. (Analytica Chimica Acta 759 (2013) 74-80). Since vasopressin is a nine amino acid hormone, like oxytocin, and differs from oxytocin by two amino acids, it is an excellent proxy for oxytocin. The vasopressin aptamer was modified with a TAMRA-modified uracil phorphoramidite, to allow the changes in the structure of the aptamer upon exposure to the target hormone to be identified: TAMRA is known to have intense Raman spectral features that compare favorably with those of FAM, and has been used in similar Raman based detection methods for vasopressin. The TAMRA-modified base was inserted at position 22 on the aptamer, the position farthest from the NP surface, which was hypothesized to produce the largest difference in TAMRA signal intensity upon exposure of the aptamer modified NPs to vasopressin.

The response of the vasopressin aptamer-modified NP were investigated in two ways. The first established the ability of aptamer-based assays to differentiate between target molecules through comparison of the changes observed upon exposure of the system to vasopressin with those observed when the system is exposed to oxytocin and substance P, a neuropeptide that is similar in length, size and mass, but not in sequence, to vasopressin. The second study established the effect of surface modification through comparison of the response observed using NPs with monolayers composed of the dye-modified aptamer alone, and the aptamer with MCP or MCH.

Figure 4A:
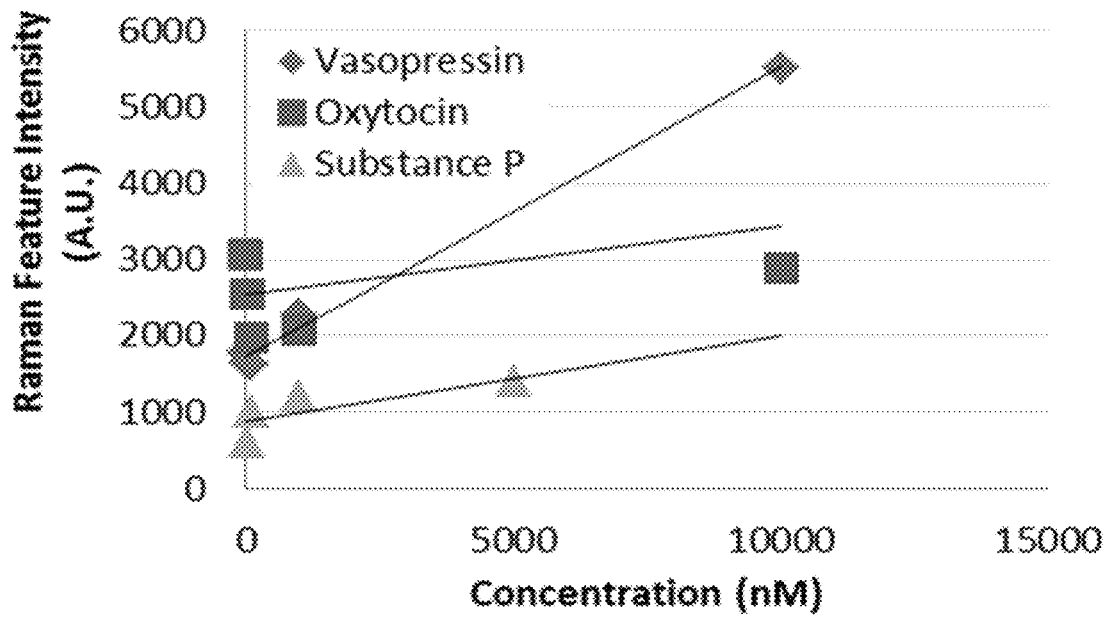
FIG. 4 contains two panels. Panel A depicts Ag NPs modified with TAMRA-containing vasopressin-targeted aptamers demonstrate selectivity for vasopressin against structurally related proteins: oxytocin and substance P. A linear correlation was observed with vasopressin ($R^2$: 0.99), whereas the interaction between substance P ($R^2$: 0.63) and oxytocin ($R^2$: 0.19) did not result in a linear correlation between concentration and spectral intensity. Panel B depicts a comparison of monolayer compositions of Ag NPs modified with TAMRA-containing vasopressin-targeted aptamers. Modification of the Ag NP surface with either the vasopressin-targeted aptamer alone, or in tandem with 40 μM MCP ($R^2$: 0.99 and 0.96, respectively), resulted in a linear correlation between vasopressin concentration and spectral feature intensity. In contrast, NPs modified with vasopressin-targeting aptamer and 4 M MCH did not result in a linear correlation ($R^2$: 0.03).
Figure 4B:
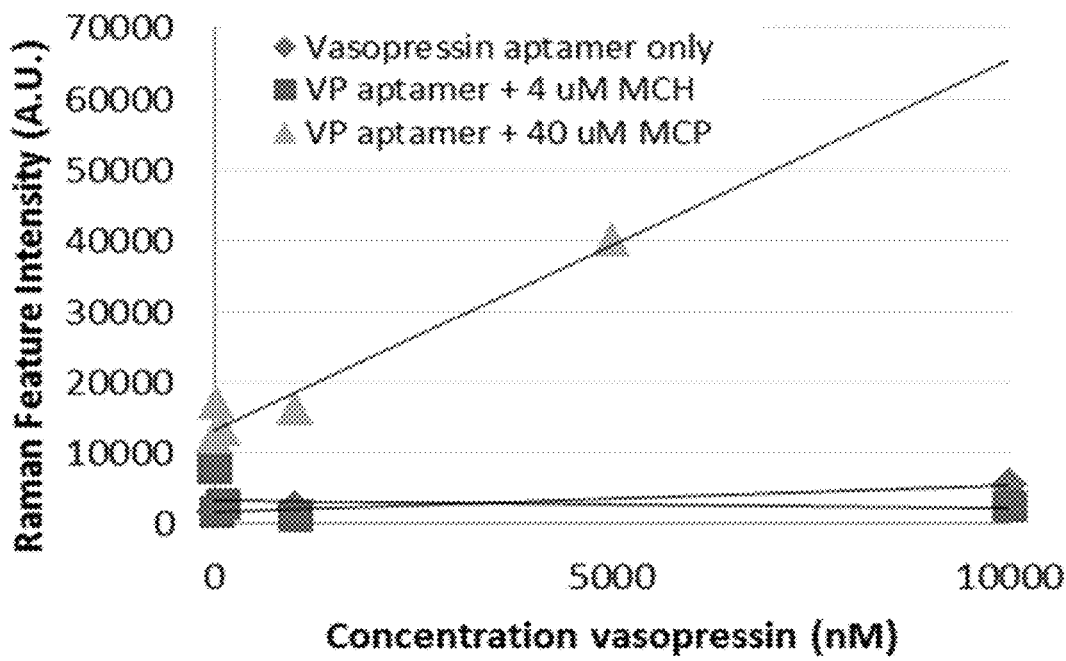

A comparison of the responses to the three proteins reveals the selectivity of the vasopressin-aptamer based SERS assay for the target molecule (FIG. 4, Panel A). Exposure of the aptamer-modified NPs to concentrations of vasopressin over a range of 1 nM to 10 µM revealed a linear increase in intensity of the 1355 $cm^{-1}$ feature in the Raman spectrum. This was not the case when the response was measured in response to exposure to a similar range of concentrations of oxytocin, where there was little correlation between the intensity of the selected feature and the concentration of the analyte. Exposure of the system to substance P revealed some correlation between concentration and feature intensity, but the correlation was not as good as that observed with the vasopressin. Surprisingly, the presence of MCP, which was intended as an internal standard against which the intensity of the Raman signal could be quantified, significantly increases the intensity of the spectral features (FIG. 4, Panel B). This effect, enhancement upon addition of a second compound to the monolayer, has been observed upon addition of MCH. However, addition of MCH in this setting did not increase the intensity of the spectral features, and dampened the response characteristics, with no correlation between VP concentration and feature intensity.

Beyond differentiation of structurally similar hormone molecules such as oxytocin and vasopressin using aptamer modified NPs, our efforts focused on improving reproducibility of spectral feature intensities, a problem that is a common to Raman-based analytical applications. Reproducibility issues, particularly with dry samples, are often associated with the presence of "hot spots", or regions where analytes lay at the junction of two Raman active NPs resulting in unusually large signal enhancement in a target for which the aptamer had been developed.

REFERENCES FOR EXAMPLES 1-4

(1) Hoon, S. et al. *BioTechniques* 2011, 51, 413.
(2) Stoltenburg, R. et al. *J Anal Methods Chem* 2012, 2012, 14.
(3) Schütze, T. et al. *PLoS ONE* 2011, 6, e29604.
(4) Latulippe, D. R. et al. *Anal. Chem.* 2013, 85, 3417.
(5) Leona, M. *Proc. Natl. Acad. Sci.* 2009, 106, 14757.
(6) O'Donnell, D. et al. *Submitt. Publ.* 2013.
(7) Navarro, J. R. G. et al. *Analyst* 2013, 138, 583.
(8) Liu, J. et al. *Nat. Protoc.* 2006, 1, 246.
(9) Thompson, D. G. et al. *Anal. Chem.* 2008, 80, 272805.
(10) Dougan, J. A. et al. *Nucleic Acids Res.* 2007, 35, 3668.
(11) Hurst, S. J. et al. *Anal. Chem.* 2006, 78, 8313.
(12) Cao, Y. C. et al. *Science* 2002, 297, 1536.
(13) Yang, J. et al. *ACS Nano* 2013, 7, 5350.

II. Reagents and Methods for Detecting Lyme Disease (Examples 5-8)

Lyme disease is caused by a variety of tick-borne pathogens, such as the gram-negative spirochete *Borrelia burgdorferi* and transmitted by Ixodid tick species. It is the leading vector-borne infectious disease in the United States, with a steady rise in number of cases reported each year. While Lyme disease symptom presentation of the classic bull's-eye rash (erythema migrans or EM rash) in endemic areas indicates immediate treatment without accompanying diagnostic testing, as many as 20% of Lyme disease cases proceed to less well diagnosed secondary symptoms without presentation or recognition of the EM rash. (Biesiada, G. et al. Arch Med Sci 2012, 8, 978).

The current CDC-approved diagnostic test is a two-tier system, consisting of an enzyme-linked immunosorbent assay (ELISA), followed by immunoblot (IB) analysis. (Ellis, D. I. et al. *Analyst* 2013, 138, 3871; Wu, X. et al. *Analyst* 2013, 138, 3005). The second tier of testing, IB analysis, is costly, time-consuming and technically challenging. The inherent flaws in the two-tiered serological Lyme testing regime include the complexity of interpreting the results and the dependence of antibody production on timing post infection (DeBiasi, R. L. et al. *Current Infectious Disease Reports* 2014, 16, 450). If the tests are given either too early (6-8 weeks post infection) or too late (4-6 months post infection), anti-Lyme antibodies may not be present at detectable levels. This is especially problematic for Lyme disease, where symptoms such as fever, joint pain, and "brain fog" are non-specific and difficult to diagnose. The clinical community feels the test is so unreliable that primary care physicians are reluctant to prescribe it, many feeling their experience with the disease and interaction with the patient is a more reliable diagnostic approach. This is a significant clinical shortcoming: accurate diagnosis of Lyme disease would allow its treatment with a short course of simple antibiotics and would prevent the costs and suffering associated with untreated cases. While numerous serological Lyme disease tests have been recently developed and are in use in the US, the new tests exhibit similar levels of false positives and/or additional false negatives due to insufficient antigen presentation; (Wu, X. et al. *Analyst* 2013, 138, 3005) none have replaced the established, CDC-approved two-tier testing format.

Low sensitivity has plagued the CDC-approved test, a flaw that has not been addressed in tests promoted as improvements over the current protocol. Irrespective of whether the low sensitivity of the assay system is due to the immune-suppressing nature of the *Borrelia* spirochete, agents secreted by the tick vector, or other unknown factors, it is clear a highly sensitive assay to detect the Lyme pathogen, *B. burgdorferi*, and other tick-borne pathogens, in human blood or serum would provide the frontline clinician with an invaluable tool in fighting this disease, a tool that is currently unavailable but is desperately needed.

Example 5

Aptamer Selection for *B. burgdorferi* Surface Protein OspA

Figure 7A:
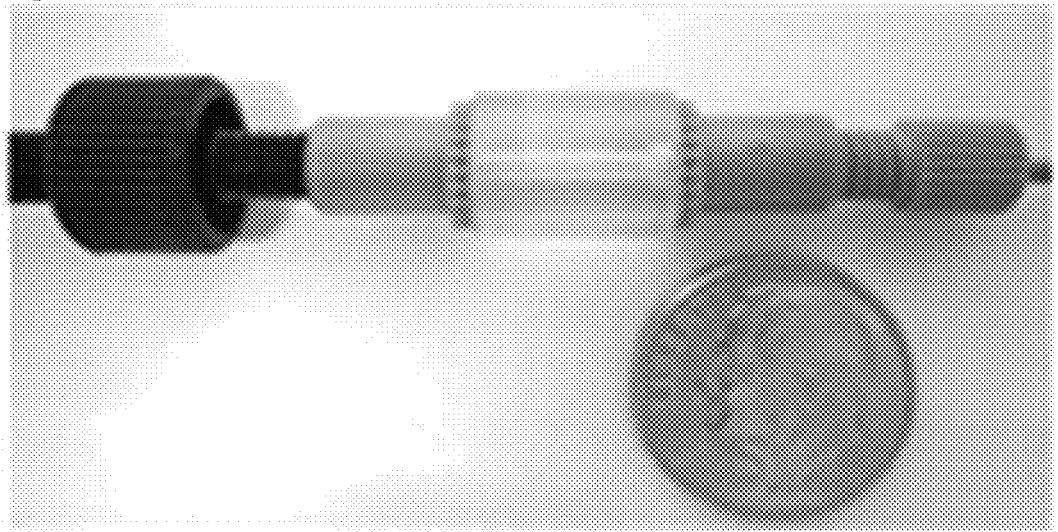
FIG. 7 contains two panels depicting aptamer selection workflow for multiple targets by use of micro-columns. Panel A shows micro-column filled with 10 μL of GFP-immobilized resin. Panel B shows multiplexed selection of RNA aptamers. The steps shown with dashed arrows are optional and are not necessarily done in each round. (Szeto, K. et al. *PLoS ONE* 2013, 8, e82667).
Figure 7B:
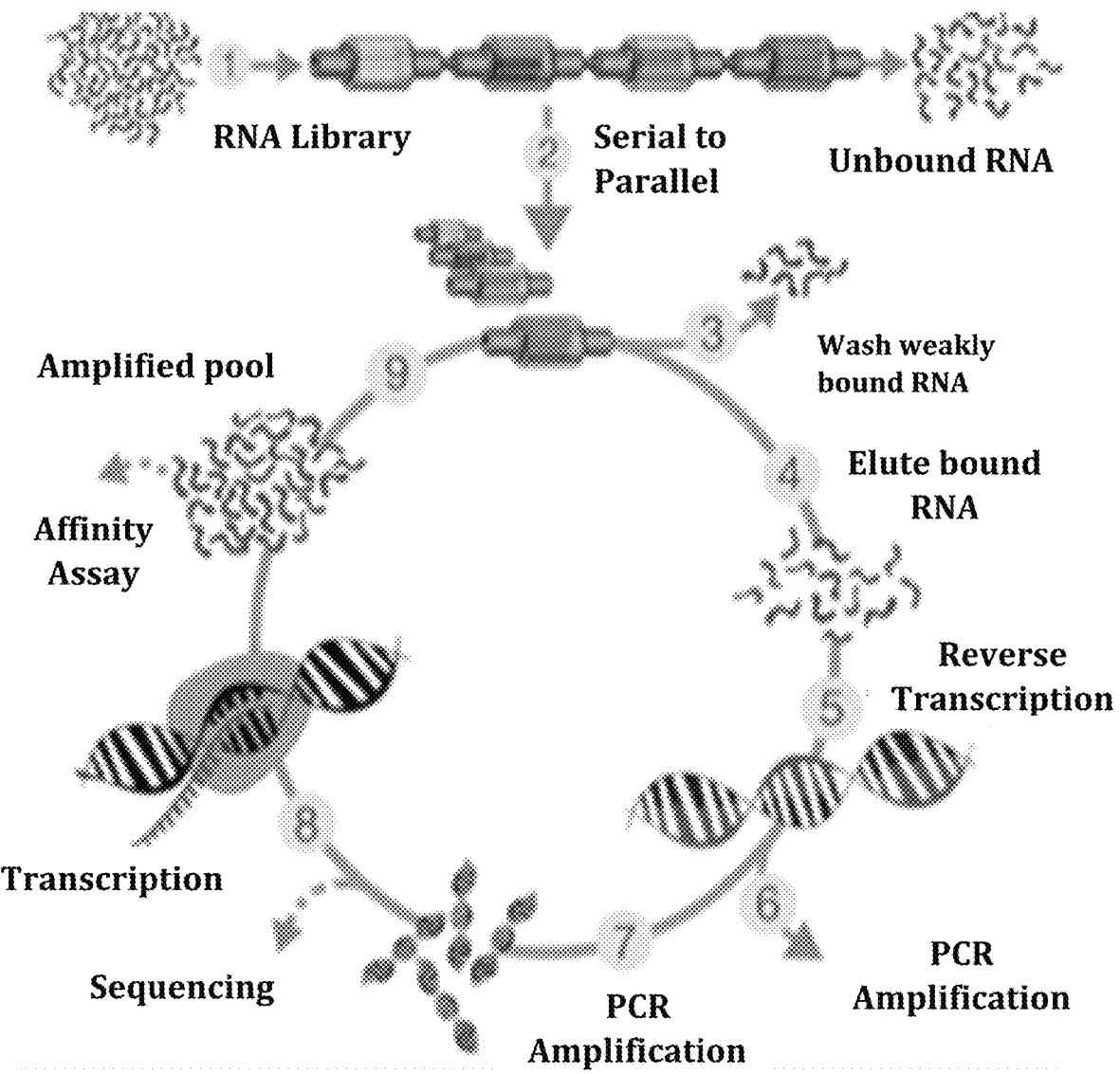

Novel, high-affinity Lyme specific aptamers were generated by employing specially designed and fabricated microcolumns (FIG. 7, Panel A). These columns were packed with target conjugated-agarose beads, or blank agarose beads (for negative selection). The columns can be run in series or in parallel, enabling efficient selection of aptamers against multiple targets simultaneously. The schematic shown in FIG. 7, Panel B illustrates the selection of RNA aptamers, though the system is readily adaptable for the generation of single-stranded DNA aptamers, simply by removing the reverse transcription and transcription steps.

The aptamer development process utilized a streamlined aptamer selection process called RNA Aptamer Isolation via Dual-cycles-SELEX (RAPID-SELEX), which eliminates unnecessary DNA amplification and purification steps. (Szeto, K. et al. *PLoS ONE* 2013, 8, e82667.) RAPID-SELEX allows aptamer pools eluted from one set of columns to be added to a second set of columns without DNA amplification between selection rounds, eliminating PCR amplification following every odd numbered round. (Szeto, K. et al. *PLoS ONE* 2013, 8, e82667.) Elimination of every other amplification and purification step reduces the average time for each round of aptamer selection by approximately 50%, and the time required for the entire selection process by 67% to 75%.

High-throughput, Next Generation DNA Sequencing (NGS) was used to determine the selected aptamer sequences from each round of microcolumn SELEX in conjunction with the Biotechnology Resource Center (BRC) and the Bioinformatics Center of Cornell University. Illumina NGS instruments were capable of generating $2\times10^7$-$2\times10^8$ DNA sequences/run, facilitating highly accurate statistical analysis of enrichment of DNA sequences by the SELEX process.

Using the methods described above, DNA aptamers that bind and detect OspA were selected: SEQ ID NOs: 67-72.

TABLE 2

OspA aptamers

| | |
|---|---|
| OspA-21 | CATGACACCGTACCTGCTCTAATAAGCACGCCAGGGACTATTAGATCGGAATAGCA CACGTCTGAACTCCAAGCACGCCAGGGACTATTA (SEQ ID NO: 67) |
| OspA-46 | CATGACACCGTACCTGCTCTAATAAGCACGCCAGGGACTATTAGATCGGAAGAGCA CACGTGTGAACTCCAAGCACGCCAGGGACTATTA (SEQ ID NO: 68) |
| OspA-22 | CATGACACCGTACCTGCTCTACGAGATTCAAGCACTCCAGGGACTATTAGATCGGA AGAGCACACGTCTGAAGCACGCCAGGGACTATTA (SEQ ID NO: 69) |
| OspA-39 | CATGACACCGTACCTGCTCTACGAGATTCAAGCACGCCAGGGATTATTAGATCGGA AGAGCACACGTCTGAAGCACGCCAGGGACTATTA (SEQ ID NO: 70) |
| OspA-55 | CATGACACCGTACCTGCTCTTGCTTTTCGTGCGCGCATAAAATACTTTGATACTGTG CCGGATGAAAGCGAAGCACGCCAGGGACTATTA (SEQ ID NO: 71) |
| OspA-59 | CATGACACCGTACCTGCTCTTGCTTTTCGTGCGCGCATAAAATACCTTGATACTGTG CCGTATGAAAGCGAAGCACGCCAGGGACTATTA (SEQ ID NO: 72) |

Figure 8:
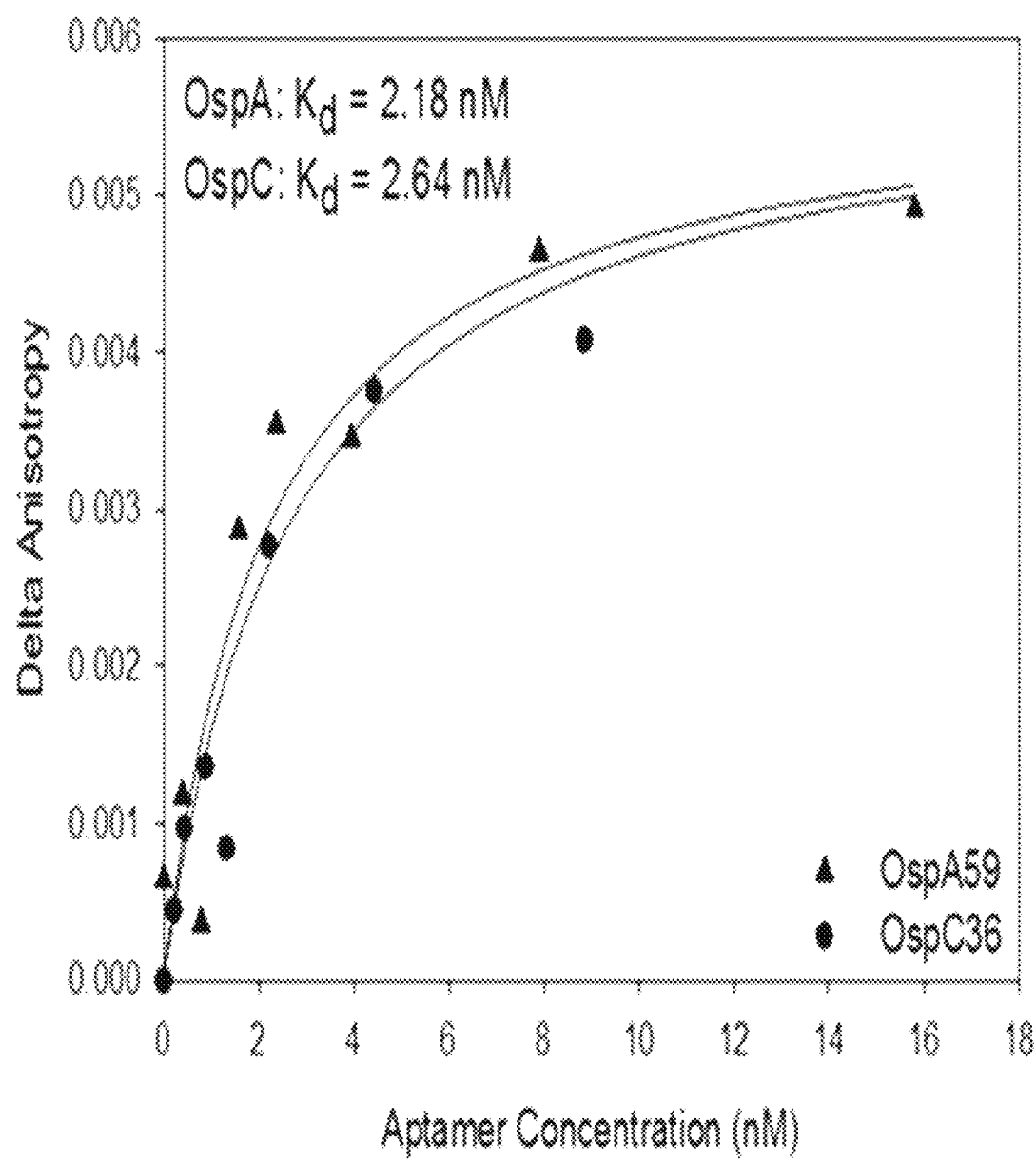
FIG. 8 depicts high affinity binding of OspA aptamer (SEQ ID NO: 4) to *B. burgdorferi* OspA protein. $K_d$ for binding is approximately 2.2 nM as determined by fluorescence anisotropy.
Figure 9A:
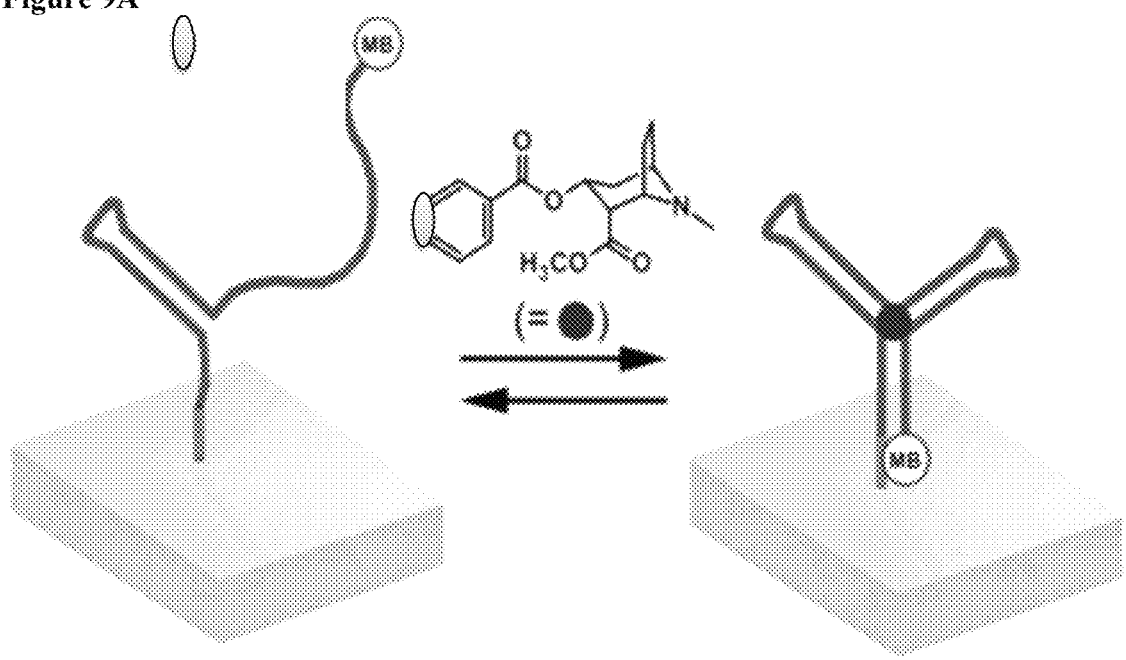
FIG. 9 contains two panels depicting the schematic representation (Panel A) and demonstration of the principle of Raman-active marker modified aptamers for detection of biological targets (Panel B). Panel A shows the Raman active dye (represented by blue circle) is brought in close proximity to the Raman substrate surface (represented by yellow block) upon exposure to the target analyte (represented by red circle). The close proximity of the dye and the SERS substrate result in high intensity SERS signals facilitating detection of the four target analytes (figure derived from: Baker, B. R. et al. *J. Am. Chem. Soc.* 2006, 128, 3138). Panel B depicts spectra demonstrating the principle—the present inventors modified a vasopressin-targeting aptamer with TAMRA, a Raman active dye. The intensity of the TAMRA Raman signal was observed to increase with concentration of the target molecule vasopressin, demonstrating the efficacy of Raman-active dye-modified aptamers in detection of biological targets.
Figure 9B:
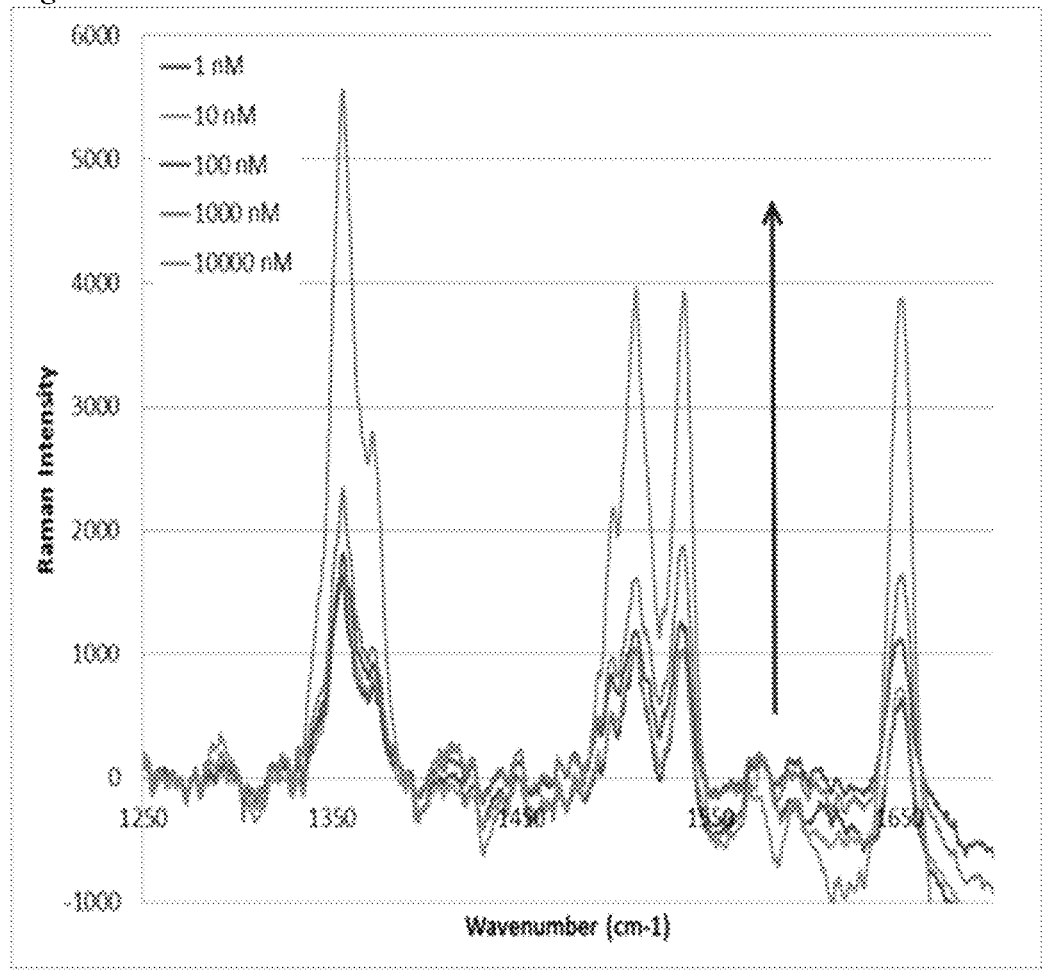
Figure 10:
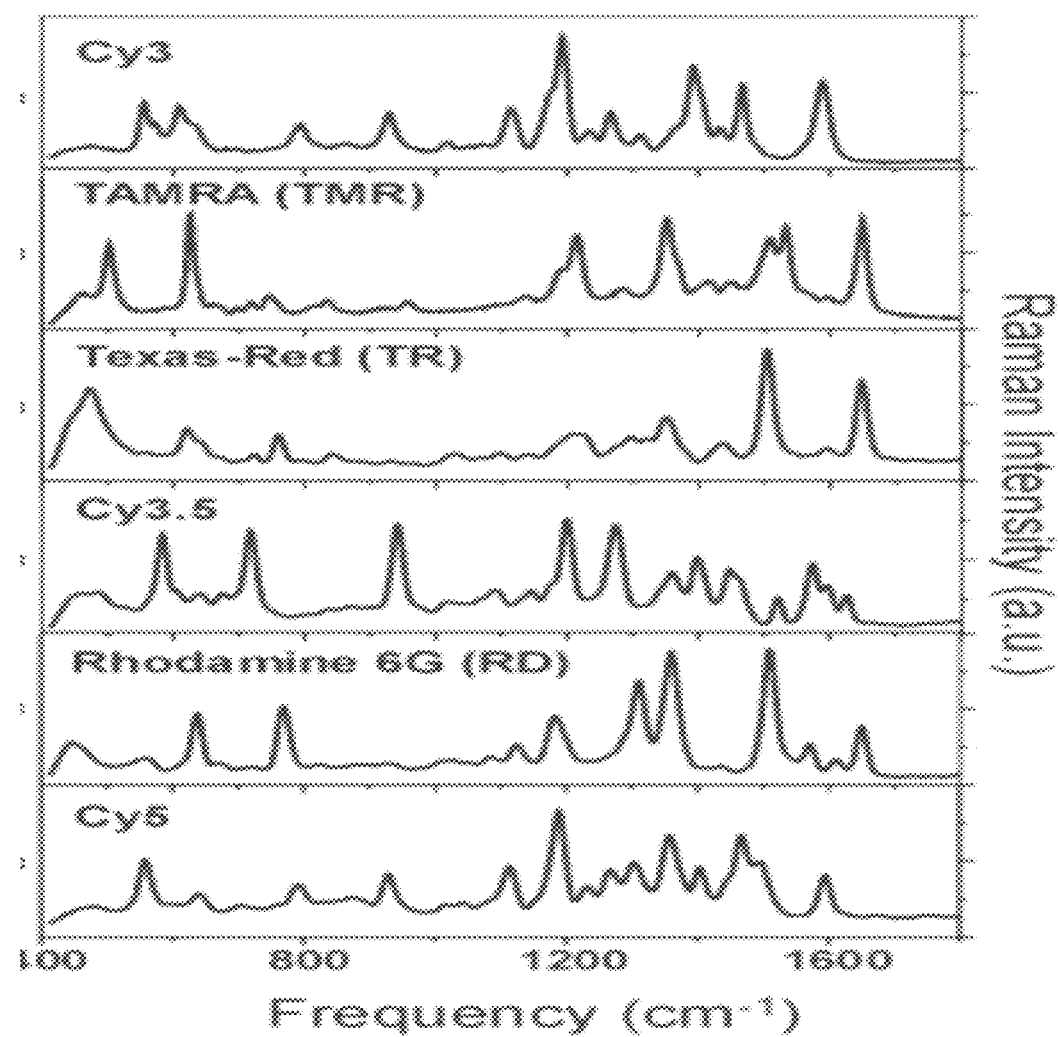
FIG. 10 depicts Raman spectra of Raman-active dyes to be employed in the multi-plex detection. Each dye serves as a proxy for each of the four target analytes, has spectral features that allow their identification in the spectra of samples containing the other dyes, and facilitate analyte detection in saliva or other biological matrices. (Cao, Y. C. et al. *Science* 2002, 297, 1536).
Figure 10:
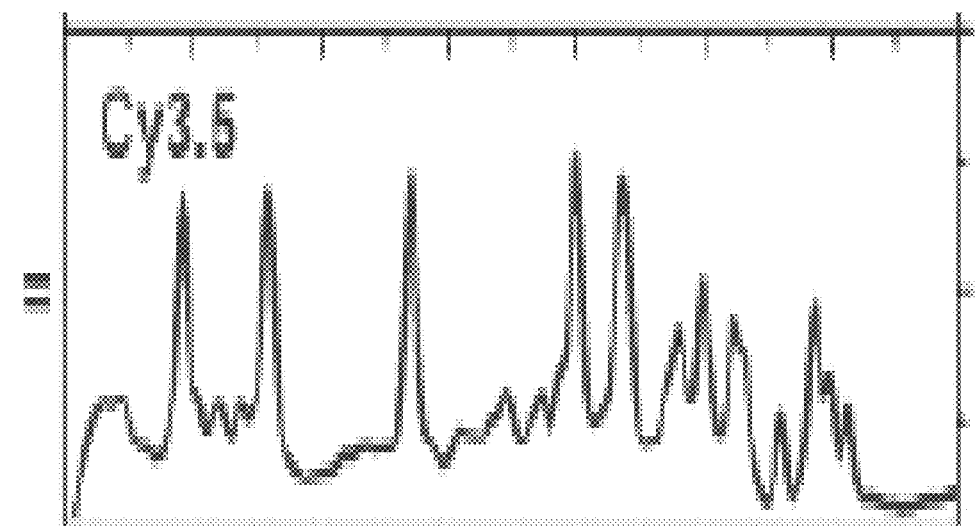

Fluorescence anisotropy was used to determine the sensitivity of the aptamers generated for Osp A. FIG. 8 shows the results of fluorescence anisotropy experiments demonstrating the binding of OspA aptamer to OspA protein. The marked increase in anisotropy with increased target protein concentrations revealed that this OspA DNA aptamer had a $K_d$=2.2 nM for OspA protein.

Aptamers specific to B. burgdorferi OspC and BmpA are generated, sequenced, and characterized using the same methods.

TABLE 3

OspC and BmpA aptamers

| | |
|---|---|
| OspC-23 | CATGACACCGTACCTGCTCTGCGGTGCTGTATCGTCGTTTAGGCTGTTACCAGGGCCAC CGGACAGAGGTAAGCACGCCAGGGACTATTA (SEQ ID NO: 73) |
| OspC-28 | CATGACACCGTACCTGCTCTCGTATAGATCCTCTCGCGCTTCGGTTTTTAGAAGTATTC AAGGTATCATCAAGCACGCCAGGGACTATTA (SEQ ID NO: 74) |
| OspC-30 | CATGACACCGTACCTGCTCTGATCAGCCTGGTCAACGGGTGGTCCTGTGCCAAGCTCG AAAATTCGCCGAAAGCACGCCAGGGACTATTA (SEQ ID NO: 75) |
| OspC-34 | CATGACACCGTACCTGCTCTTGGAGCTAGAGAGCCGGTGATCGAAATTCTGGATGTTTC TGACGTTTGCTAAGCACGCCAGGGACTATTA (SEQ ID NO: 76) |
| OspC-36 | CATGACACCGTACCTGCTCTACCCCGGAAATGATTAGCCATTGTGGTACTCATCTGGGC AGTCAGCACATAAGCACGCCAGGGACTATTA (SEQ ID NO: 77) |
| OspC-37 | CATGACACCGTACCTGCTCTTTAACCCCTCGCGGAGGTGTACACGGGCCTACATAATCC TCCGAGGTTCCAAGCACGCCAGGGACTATTA (SEQ ID NO: 78) |
| BmpA-5 | CATGACACCGTACCTGCTCTTTACGTTTGGGACGTCTGGCGAAGCCACCACAAGCTAG CCCTCCAATTTAAAGCACGCCAGGGACTATTA (SEQ ID NO: 79) |
| BmpA-6 | CATGACACCGTACCTGCTCTTTGATCATCACGGCACACTCATTACGGTTGGATATACTA GTCCGGTTAGAAAGCACGCCAGGGACTATTA (SEQ ID NO: 80) |
| BmpA-7 | CATGACACCGTACCTGCTCTCCCTTCTGACTGGATGCCGGATCTGGGCCGATTTTGTTC GCGCCCCGCCCAAGCACGCCAGGGACTATTA (SEQ ID NO: 81) |
| BmpA-8 | CATGACACCGTACCTGCTCTTTCCGCTGGTTCCACGTGGTCCCGCGTAGGTTCGTGTGC GCGCAAAATCCAAGCACGCCAGGGACTATTA (SEQ ID NO: 82) |
| BmpA-9 | CATGACACCGTACCTGCTCTGCCCCTGCGTGCCGCAGTCAATCACCATGTTGTTATTAC GGACTACCTGGAAGCACGCCAGGGACTATTA (SEQ ID NO: 83) |
| BmpA-10 | CATGACACCGTACCTGCTCTCCGGTACGATAGGGGTTGAGTTGGACACACTGCCTGGTT AAATTGTGCAGAAGCACGCCAGGGACTATTA (SEQ ID NO: 84) |

Fluorescence anisotropy can be complemented with EMSA and microplate capture assays to allow binding affinity of DNA aptamers for their targets.

Example 6

Characterization of OspA, OspC and BmpA Aptamer Binding to Target Proteins

Methods necessary to detect and quantify the binding affinity of individual aptamers to specific *B. burgdorferi* proteins are developed. A variety of method can be used to demonstrate target binding to potential DNA aptamer oligonucleotides. While electrophoretic mobility shift assay (EMSA); fluorescence anisotropy measurements; DNA pull-down assays; microplate capture assays can be used to determine aptamer affinity for its targets, the inventors effectively employed fluorescence anisotropy to determine the sensitivity of aptamers generated for OspA (FIG. 8). Briefly, fluorescently labeled target protein, in this case either OspA or OspC were assayed against increasing concentration of target specific aptamer. Changes in the rotational speed of the fluorescent proteins upon aptamer binding were detected through changes in the polarizability of the dye emissions, providing a rapid and reliable test to determine the affinity of the aptamer for its target. The marked increase in anisotropy with increased target protein concentrations revealed the OspA aptamer to bind with a $K_d$ of approximately 2.2 nM.

Anisotropy measurements of fluorescently labelled proteins are most effective when aptamer binding significantly increases the size of the complex, resulting in a significant decrease in the rate of rotation of the aptamer in solution. While fluorescence anisotropy employed effectively to determine the $K_d$ of the OspA aptamer for its target, this is not true for all aptamer-target interactions. Should fluorescence anisotropy not prove effective, EMSA and microplate capture assays to allow binding affinity of DNA aptamers for their targets can be utilized.

To identify aptamers with the highest affinity for the three target proteins, up to six of the most commonly aptamer sequences for each *B. burgdorferi* protein are synthesized and screened. Concentrations ranging from 0.1 nM to 100 nM Lyme-specific aptamer are used for these experiments; binding affinities of <1 nM to 5 nM are considered adequate for use. The 1 or 2 aptamers with the highest affinities for their specific target are employed in the Examples 7 and 8.

Example 7

Detection of *B. burgdorferi* Proteins by SERS

Nanoparticles are modified with the thiolated aptamers (ApNPs) optimized in Example 5 for capture and detection of *B. burgdorferi*-specific OspA, OspC, and BmpA proteins. The Ag nanoparticle are synthesized using a simple, established literature procedure involving reduction of a silver nitrate solution with sodium citrate under microwave irradiation (Leona, M. *Proc. Natl. Acad. Sci.* 2009, 106, 14757) or Au NPs purchased from a commercial source (e.g. Ted Pella; Redding, Calif.; or Nanopartz, Loveland, Colo.).

Surface modification with the aptamers is executed through standard thiol-metal interactions, and the concentration of aptamers appropriate for the target NP size are calculated using Eqn. 1. (Taton, T. A. *In Current Protocols in Nucleic Acid Chemistry*; John Wiley & Sons Inc.: New York, 2002).

$$\text{Amt of aptamer}=A_n \times C_n \times D_o \times V \quad (1)$$

$A_n$=NP surface area ($cm^{-2}$); $C_n$=particle conc. (particles $L^{-1}$); $D_o$=Ap density (mol $cm^{-2}$); V=reaction vol. (L)

To determine the efficiency of surface modification, fluorophore-modified Lyme-specific aptamers are employed in the fluorometric quantitation technique developed by Mirkin and co-workers. (Demers, L. M. et al. *Anal Chem* 2000, 72, 5535).

The aptamers developed in Example 5 are modified with Raman-active dyes that served as proxies for the target molecule. This is schematically represented in FIG. 9, Panel A. (figure derived from: Baker, B. R. et al. *J. Am. Chem. Soc.* 2006, 128, 3138) To demonstrate the principle, an aptamer developed for targeting vasopressin was modified with TAMRA, a molecule known to have a strong Raman signal (FIG. 10). (Cao, Y. C., et al. *Science* 2002, 297, 1536). The intensity of the Raman signal increased in concert with the concentration of vasopressin, demonstrating the principle of Raman active dyes being used as proxies for the target molecule. Exposure of this TAMRA-modified aptamer to similar polypeptides (i.e. substance P and oxytocin; data not shown) not result in a significant increase in Raman signal intensity, demonstrating that the aptamer-based SERS-detection approach was capable of both detecting its target and differentiating the target from molecules with significant structural similarity.

While FIG. 9, Panel B demonstrates the principle of dye-modified aptamers as recognition elements, the placement of the dye in the sequence, and the identity of the dye can provide optimal sensitivity for the Lyme disease-related proteins. Each aptamer developed in Example 5 is modified with a Raman-active marker in the terminal position and at multiple internal positions. The dyes are selected for high signal intensity (e.g., FAM, Cy3, Cy 3.5, Cy5 and TAMRA), and distinct spectral features that allowed them to easily be identified (FIG. 10). (Cao, Y. C. et al. *J. Am. Chem. Soc.* 2002, 125, 14676). The Raman-active dyes are incorporated into the aptamer DNA sequences during oligonucleotide synthesis using commercial reagents.

Raman investigations are initiated using research grade instrumentation to optimize the spectroscopic method. These methods are then be re-tested using a portable, commercially available spectrometer using 785 nm incident light, a wavelength frequently used in portable commercial bench top or handheld Raman spectrometers.

Each of the aptamer-modified NPs is exposed to a solution containing one of the *B. burgdorferi*-specific proteins for which it is designed, allowing the aptamer to capture the target. This process is repeated with each of the ApNPs in the presence of the *B. burgdorferi* proteins for which the aptamer is not developed, to demonstrate specificity of the ApNPs for their target molecules. To optimize incubation conditions for target capture, three variables are investigated: aptamer concentration at the NP surface, concentration and composition of additives intended to stabilize and optimize Raman spectral features, and incubation time of the ApNPs with the target metabolites. The optimal combination of aptamer concentration at the NP surface, and incubation time are investigated to determine the limit of detection for each of the analytes. The limit of detection established in these investigations are compared with the sensitivity of established standard biological assays, such as commercial Lyme immunoassays (e.g. ELISA), providing a value against which subsequent investigations can be compared.

Other surface modifications may be performed. For example the surface modifications may include PEG to coat parts of the nanoparticle surface not covered by aptamers. Alternatively, the surface modifications may include alkyl thiols.

Example 8

Rapid Detection of *B. burgdorferi* Proteins Human Lyme Disease Serum Panels

Rapid detection of *B. burgdorferi* proteins in human Lyme disease serum panels is performed in collaboration with Clinical and Translational Science Center and the Joint Clinical Trials Office at Weill Cornell Medical College. Human serum panels are obtained from two separate sources: a commercially available Lyme disease serum panel from SeraCare, a company that provides human serum panels for a variety of infectious and other disease states; and Lyme disease serum panels available from the US CDC (Molins, 2014 doi:10.1128/JCM.01409-14). These panels include serum from uninfected individuals and from individuals infected with *B. burgdorferi* at various stages of disease. These panels are ideal for pre-clinical testing.

For these studies, 5-10 μL of human serum, either negative control or Lyme positive samples are diluted into buffer and mixed with ApNPs as described in Example 6. Following binding of the ApNPs to the *B. burgdorferi* target proteins, the samples are divided in half; one aliquot is analyzed for SERS in a bench top Raman spectrometer, and the second is reserved for analysis using commercial *B. burgdorferi* immunoassays. The panels referenced above include serum from uninfected individuals and are used as negative controls. In these studies, a number of variables are directly studied, including: the time required for optimum binding; the concentration of ApNPs required for optimal signal; minimal amount of human serum necessary for detection of the *B. burgdorferi* proteins; and the relative sensitivities of the OspA, OspC, and BmpA assays. The sensitivity and specificity of the SERS-based *B. burgdorferi* assays are determined. A variety of statistical analyses are used to determine the best diagnostic models and cut-off required to optimize *B. burgdorferi* detection in humans.

Rapid Detection of *B. burgdorferi* Proteins from Infected *Ixodes scapularis* Ticks Assays developed in Examples 5, 6, and 7 are used to demonstrate the detection of *B. burgdorferi* in infected *I. scapularis* ticks. Ticks obtained from two separate sources are used. Control, non-infected *I. scapularis* tick nymphs are purchased from the Oklahoma State University Tick Rearing Facility. The Tick Rearing facility is a fee-for-service facility that provides uninfected, laboratory raised ticks at various life cycle stages for research applications.

Wild *B. burgdorferi*-infected ticks are collected in collaboration with the Department of Natural Resources at Cornell University. The effects of environmental conditions on the survival of *I. scapularis* in their habitat are studied. Ticks are collected as follows: *Ixodes scapularis* nymphs are collected from the field between May and July during their seasonal activity peak. (Falco, R. C. et al. *Am. J. Epidemiol.* 1999, 149, 771) A well-established drag sampling method is used to collect them: a white cloth with an area of one square meter is dragged over vegetation and leaf litter in forested areas. (Schulze, T. L. et al. *J. Med. Entomol.* 1997, 34, 615.) The cloth mimics the animal hair fibers to which *I. scapularis* attaches itself. Nymphs are stored at −80° C. at the Cary Institute until they can be used for further analysis. Studies from the Cary Institute show that as many as 55% of *I. scapularis* nymphs collected in the Hudson River Valley of New York are infected with *B. burgdorferi*. (Aliota, M. T. et al. *Vector Borne Zoonotic Dis. Larchmt.* N 2014, 14, 245)

Between 5 and 10 tick nymphs, either lab reared or collected, are lysed by placing them in a micro centrifuge tube and homogenized with a disposable homogenizer in buffered lysing solution. Once the ticks are ruptured, aliquots of the homogenate are briefly centrifuged to remove debris and the extract is mixed with ApNPs as described in Example 7. Following binding of the ApNPs to the *B. burgdorferi* target proteins, the samples are divided in half; one aliquot is analyzed for SERS in a bench top Raman spectrometer, and the second is reserved for analysis using commercial *B. burgdorferi* immunoassays. Lab raised tick nymphs obtained from the Oklahoma State University Tick Rearing Facility serve as negative controls.

A number of variables are directly studied, including: the time required for optimum binding; the concentration of ApNPs required for optimal signal; minimal number of infected nymphs necessary for detection of the Osp proteins; and the relative sensitivities of the OspA, OspB, and OspC assays. The sensitivity and specificity of the SERS-based *B. burgdorferi* assays are determined.

INCORPORATION BY REFERENCE

The contents of all references, patent applications, patents, and published patent applications, as well as the Figures and the Sequence Listing, cited throughout this application are hereby incorporated by reference in their entirety as if each individual publication or patent was specifically and individually incorporated by reference. In case of conflict, the present application, including any definitions herein, may control.

EQUIVALENTS

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention may become apparent to those skilled in the art upon review of this specification. The full scope of the invention should be determined by reference to the claims, along with their full scope of equivalents, and the specification, along with such variations. Such equivalents are intended to be encompassed by the following claims

What is claimed:

1. A method for determining the presence of one or more OspA analyte in a biological sample, the method comprising:
   a) receiving the biological sample;
   b) contacting the biological sample to at least one SERS-active reagent, said reagent:
      (i) comprises one or more SERS-active surface which is covalently-modified with one or more dithiol-modified single stranded DNA aptamer comprising the nucleotide sequence of SEQ ID NO: 71 or 72: and
      (ii) said one or more aptamer is covalently attached via a modified base to one or more Raman-active marker;
   c) allowing the one or more OspA analyte to come into contact with the one or more aptamer;
   d) binding of the one or more OspA analyte to the one or more aptamer, wherein said binding causes the one or more aptamer to undergo a conformational change, thereby forming at least one SERS-active reagent bound to the one or more OspA analyte, wherein the conformational change in the one or more aptamer upon binding of the one or more OspA analyte brings the one or more Raman-active marker into closer proximity to the one or more SERS-active surface relative to the unbound aptamer conformation, and leads to a change in a Raman signal;
   e) irradiating the at least one SERS-active reagent bound to the one or more OspA analyte to generate the Raman signal;
   f) detecting the Raman signal of the at least one SERS-active reagent bound to the one or more OspA analyte to generate Raman spectra; and
   g) comparing the Raman spectra detected in (f) to reference Raman spectra of a control, wherein the presence of one or more OspA analyte in the biological sample is determined when said Raman spectra detected in (f) differ from said reference Raman spectra in positions and/or intensities.

2. The method of claim 1, wherein a difference in the Raman spectra in (g) when compared to control can be correlated with the amount of the one or more OspA analyte.

3. A method for diagnosing a *B. burgdorferi* infection in a subject comprising the steps of:
   a) receiving a biological sample from the subject;
   b) contacting the biological sample to at least one SERS-active reagent, said reagent:
      (i) comprises one or more SERS-active surface;
      (ii) which is covalently-modified with one or more dithiol-modified single-stranded DNA comprising the nucleotide sequence of SEQ ID NO: 71 or 72; and
      (iii) said one or more aptamer is covalently attached via a modified base to one or more Raman-active marker;
   c) allowing binding of the at least one SERS-active reagent to one or more OspA analyte in the biological sample, wherein said binding causes a conformational change to the one or more aptamer of the at least one SERS-active reagent, thereby forming at least one SERS-active reagent bound to the one or more OspA analyte, wherein the conformational change in the one or more aptamer upon binding of the one or more OspA analyte brings the one or more Raman-active marker into closer proximity to the one or more SERS-active surface relative to the unbound aptamer conformation, and leads to a change in a Raman signal;
   d) irradiating the at least one SERS-active reagent bound to the one or more OspA analyte to generate the Raman signal;
   e) detecting the Raman signal of the at least one SERS-active reagent bound to the one or more OspA analyte to generate Raman spectra; and
   f) comparing the Raman spectra detected in (e) to reference Raman spectra of said at least one SERS-active reagent detected in a laboratory derived negative control sample, biological sample received from a control subject (healthy subject), or pooled biological samples from numerous control subjects (healthy subjects), wherein said *B. burgdorferi* infection is diagnosed when said Raman spectra detected in (e) differ from said reference Raman spectra in positions and/or intensities.

4. The method according to claim 1, wherein the one or more SERS-active surface is selected from the group consisting of silver, gold, Cu, titanium nitride, titanium oxide, zinc oxide, zinc selenide, graphene, and molybdenum disulfide.

5. The method according to claim 1, wherein the Raman-active marker comprises a dye, fluorescent marker, carbon nanotubes, fullerenes, alkene, alkyne, or azide.

6. The method according to claim 1, wherein the Raman-active marker is a fluorescent or non-fluorescent Raman-sensitive marker, and said marker is selected from the group consisting of azides, alkynes, fluorescein (FAM), Carboxytetramethylrhodamine (TAMRA), Cy3, Texas-Red (TR), Cy3.5, Rhodamine 6G, Cy5, TRIT (tetramethyl rhodamine isothiol), NBD (7-nitrobenz-2-oxa-1,3-diazole), phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and quantum dots.

7. The method according to claim 1, wherein the OspA analyte is selected from the group consisting of peptide, polypeptide, protein, and lipoprotein.

8. The method according to claim 3, wherein the one or more SERS-active surface is selected from the group consisting of silver, gold, Cu, titanium nitride, titanium oxide, zinc oxide, zinc selenide, graphene, and molybdenum disulfide.

9. The method according to claim 3, wherein the Raman-active marker comprises a dye, fluorescent marker, carbon nanotubes, fullerenes, alkene, alkyne, or azide.

10. The method according to claim 3, wherein the Raman-active marker is a fluorescent or non-fluorescent Raman-sensitive marker, and said marker is selected from the group consisting of azides, alkynes, fluorescein (FAM), Carboxytetramethylrhodamine (TAMRA), Cy3, Texas-Red (TR), Cy3.5, Rhodamine 6G, Cy5, TRIT (tetramethyl rhodamine isothiol), NBD (7-nitrobenz-2-oxa-1,3-diazole), phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and quantum dots.

11. The method according to claim 3, wherein the OspA analyte is selected from the group consisting of peptide, polypeptide, protein, and lipoprotein.

\* \* \* \* \*